United States Patent [19]
Plyley et al.

[11] Patent Number: 5,489,058
[45] Date of Patent: Feb. 6, 1996

[54] SURGICAL STAPLER WITH MECHANISMS FOR REDUCING THE FIRING FORCE

[75] Inventors: Alan K. Plyley; Claude A. Vidal, both of Santa Barbara; Russell J. Redmond, Goleta; John L. Minck, Jr., Santa Barbara, all of Calif.; Alan J. Solyntjes, Richfield, Minn.

[73] Assignee: Minnesota Mining and Manufacturing Company, St. Paul, Minn.

[21] Appl. No.: 236,379

[22] Filed: May 2, 1994

[51] Int. Cl.⁶ .................................................. A61B 17/068
[52] U.S. Cl. ........................ 227/176.1; 227/19; 227/178.1
[58] Field of Search ..................................... 227/175, 176, 227/178, 179, 180, 181, 19

[56] References Cited

U.S. PATENT DOCUMENTS

| | | |
|---|---|---|
| 2,142,782 | 1/1939 | Gillette . |
| 2,174,219 | 9/1939 | Balma . |
| 2,246,647 | 6/1941 | Vancura . |
| 3,079,606 | 3/1963 | Bobrov et al. . |
| 3,275,211 | 9/1966 | Hirsch et al. . |
| 3,315,863 | 4/1967 | O'Dea . |
| 3,490,675 | 1/1970 | Green et al. . |
| 3,494,533 | 2/1970 | Green et al. . |
| 3,499,591 | 3/1970 | Green . |
| 3,692,224 | 9/1972 | Astafiev et al. ........................... 227/19 |
| 3,844,289 | 10/1974 | Noiles .................................... 128/334 R |
| 4,086,926 | 5/1978 | Green et al. ......................... 128/334 R |
| 4,202,480 | 5/1980 | Annett ....................................... 227/8 |
| 4,256,251 | 3/1981 | Moshofsky .............................. 227/120 |
| 4,261,244 | 4/1981 | Becht et al. ............................. 411/472 |
| 4,304,236 | 12/1981 | Conta et al. ............................ 128/325 |
| 4,305,539 | 12/1981 | Korolkov et al. .......................... 227/8 |
| 4,391,401 | 7/1983 | Moshofsky ................................ 227/19 |
| 4,402,444 | 9/1983 | Green ....................................... 227/19 |
| 4,415,112 | 11/1983 | Green ....................................... 227/19 |
| 4,429,695 | 2/1984 | Green ..................................... 128/305 |
| 4,473,077 | 9/1984 | Noiles et al. ........................... 128/305 |
| 4,519,532 | 5/1985 | Foslien ...................................... 227/8 |
| 4,520,817 | 6/1985 | Green ..................................... 128/305 |
| 4,527,724 | 7/1985 | Chow et al. ............................... 227/8 |
| 4,569,346 | 2/1986 | Poirier ................................... 128/305 |
| 4,576,167 | 3/1986 | Noiles ................................. 128/334 R |
| 4,591,085 | 5/1986 | Di GIovanni ............................. 227/8 |
| 4,596,351 | 6/1986 | Fedotov et al. ........................... 227/19 |
| 4,605,001 | 8/1986 | Rothfuss et al. ...................... 128/305 |
| 4,607,638 | 8/1986 | Crainich ................................ 128/335 |

(List continued on next page.)

FOREIGN PATENT DOCUMENTS

| | | |
|---|---|---|
| 54764/86 | 9/1986 | Australia . |
| 54765/86 | 9/1986 | Australia . |
| 72196/87 | 11/1987 | Australia . |
| 0380025 | 8/1990 | European Pat. Off. . |
| 0449394 | 10/1991 | European Pat. Off. . |
| 0484677 | 5/1992 | European Pat. Off. . |
| 0489436 | 6/1992 | European Pat. Off. . |
| 0503662 | 9/1992 | European Pat. Off. . |
| 0505036 | 9/1992 | European Pat. Off. . |
| 0514139 | 11/1992 | European Pat. Off. . |
| 0517975 | 12/1992 | European Pat. Off. . |
| 0537572 | 4/1993 | European Pat. Off. . |
| 0539762 | 5/1993 | European Pat. Off. . |
| 0541950 | 5/1993 | European Pat. Off. . |
| 0545029 | 6/1993 | European Pat. Off. . |
| 0579038 | 1/1994 | European Pat. Off. . |
| 0593920 | 4/1994 | European Pat. Off. . |
| 0598202 | 5/1994 | European Pat. Off. . |
| 0406832 | 12/1924 | Germany . |
| 2744824 | 2/1980 | Germany . |
| 3819293 | 7/1989 | Germany . |
| 2070499 | 9/1981 | United Kingdom . |
| WO93/02247 | 7/1983 | WIPO . |
| WO92/10976 | 7/1992 | WIPO . |

Primary Examiner—Scott A. Smith
Attorney, Agent, or Firm—Gary L. Griswold; Walter N. Kirn; Jeffrey J. Hohenshell

[57] ABSTRACT

Surgical staplers for use during open and/or laparoscopic surgical procedures are disclosed. Novel firing device trapping assemblies, pushers, staple lines and firing handles are described. Many of the novel devices reduce the overall firing force experienced by the surgeon.

7 Claims, 28 Drawing Sheets

U.S. PATENT DOCUMENTS

| | | | |
|---|---|---|---|
| 4,608,981 | 9/1986 | Rothfuss et al. | 128/305 |
| 4,632,290 | 12/1986 | Green et al. | 227/19 |
| 4,633,861 | 1/1987 | Chow et al. | 128/305 |
| 4,633,874 | 1/1987 | Chow et al. | 128/334 R |
| 4,646,745 | 3/1987 | Noiles | 128/334 R |
| 4,664,305 | 5/1987 | Blake, III et al. | 227/19 |
| 4,767,044 | 8/1988 | Green | 227/19 |
| 4,809,898 | 3/1989 | Gassner et al. | 227/8 |
| 4,848,637 | 7/1989 | Pruitt | 227/19 |
| 4,863,088 | 9/1989 | Redmond et al. | 227/19 |
| 4,869,415 | 9/1989 | Fox | 227/19 |
| 4,892,244 | 7/1990 | Fox et al. | 227/8 |
| 4,938,408 | 9/1990 | Bedi et al. | 227/8 |
| 4,941,623 | 7/1990 | Pruitt | 227/19 |
| 4,955,959 | 9/1990 | Tompkins et al. | 227/178 |
| 4,978,049 | 12/1990 | Green | 227/178 |
| 5,031,814 | 7/1991 | Tompkins et al. | 227/8 |
| 5,071,052 | 12/1991 | Rodak et al. | 227/178 |
| 5,083,695 | 1/1992 | Foslien et al. | 227/8 |
| 5,106,008 | 4/1992 | Tompkins et al. | 227/178 |
| 5,111,987 | 5/1992 | Moeinzadeh et al. | 227/180 |
| 5,129,570 | 7/1992 | Schulze et al. | 227/19 |
| 5,141,144 | 8/1992 | Foslien et al. | 227/176 |
| 5,221,036 | 6/1993 | Takase | 227/19 |
| 5,222,975 | 6/1993 | Crainich | 606/219 |
| 5,253,793 | 10/1993 | Green et al. | 227/178 |
| 5,258,009 | 11/1993 | Conners | 606/219 |
| 5,307,979 | 5/1994 | Olson et al. | 227/178 |
| 5,318,221 | 6/1994 | Green et al. | 227/178 |
| 5,332,142 | 7/1994 | Robinson et al. | 227/178 |
| B1 4,892,244 | 8/1991 | Fox et al. | 227/8 |

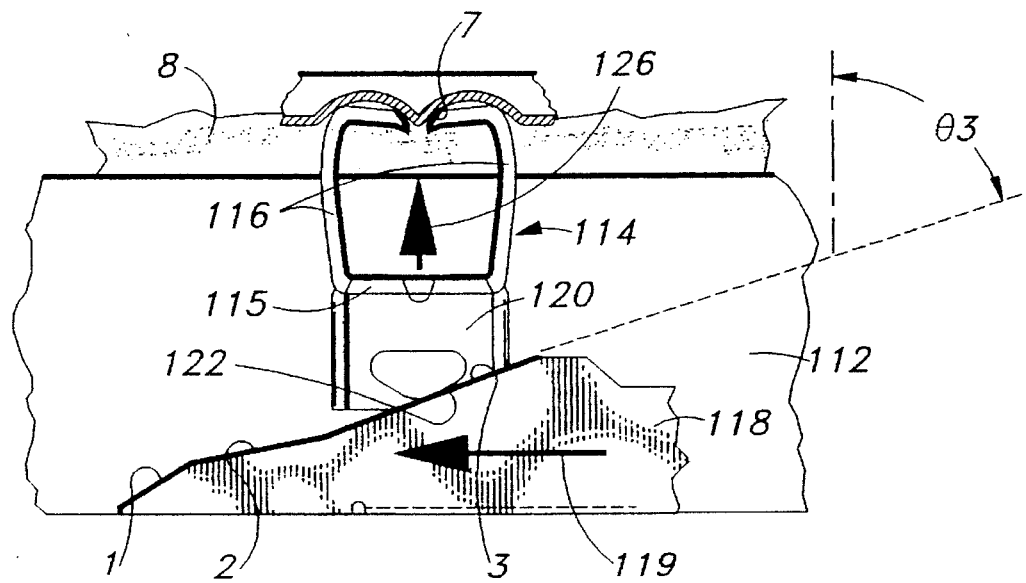
FIG. 15
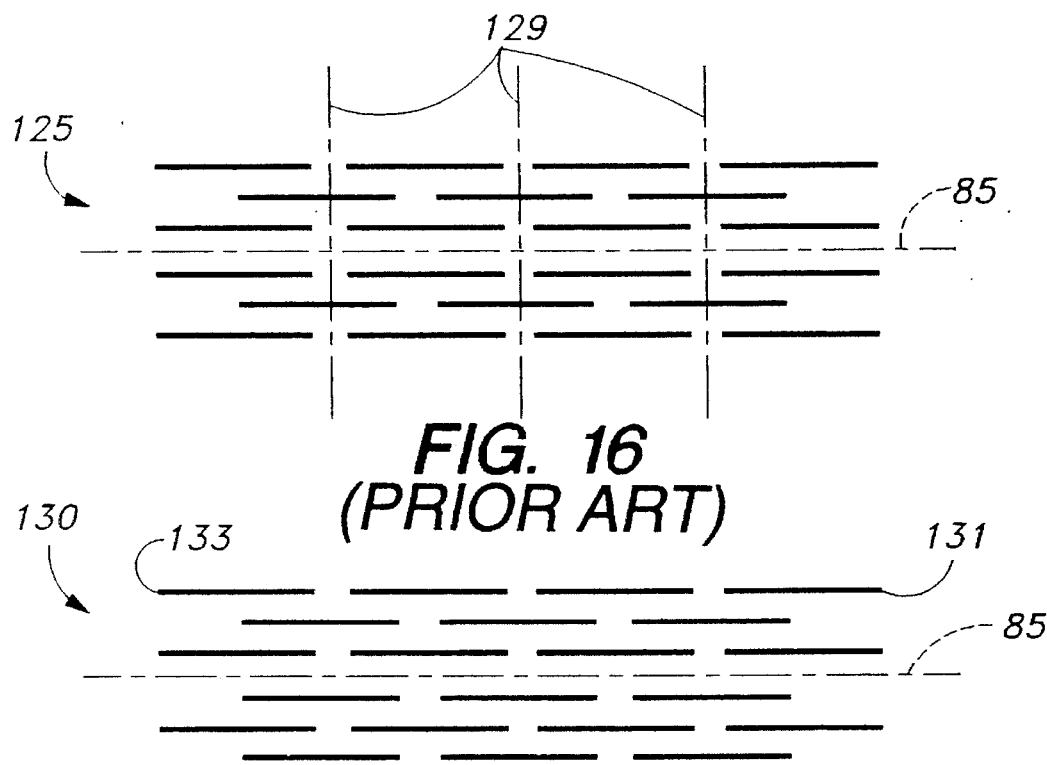
FIG. 16
(PRIOR ART)
FIG. 17

H=0
MF=0

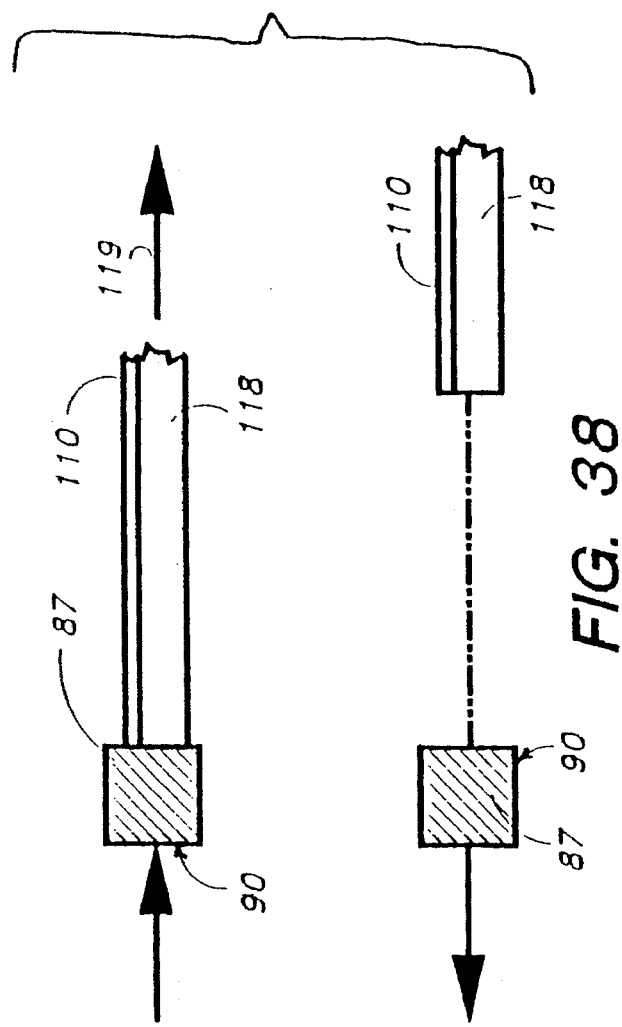
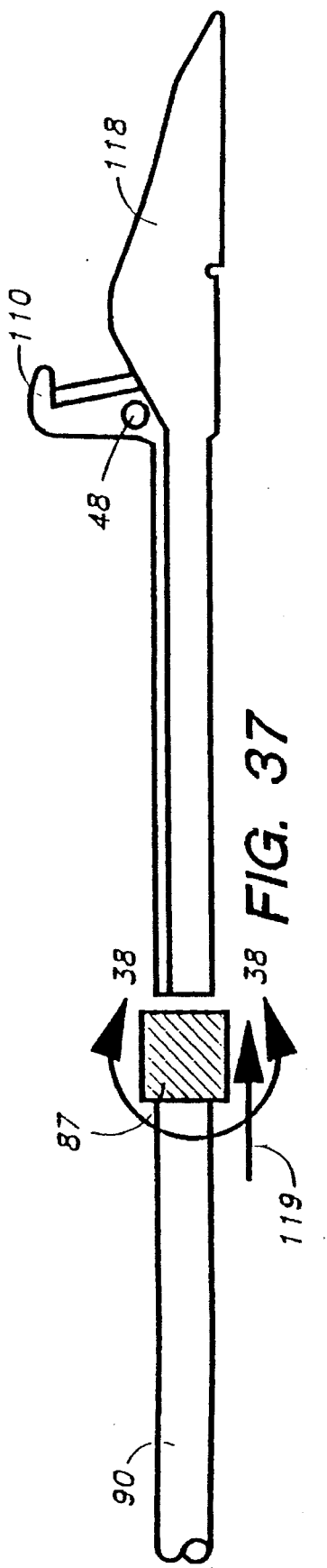
FIG. 38
FIG. 37

SURGICAL STAPLER WITH MECHANISMS FOR REDUCING THE FIRING FORCE

TECHNICAL FIELD

The present invention relates generally to surgical stapling instruments used in open and/or laparoscopic surgical procedures and more particularly to the type of surgical stapling instruments used for substantially sequentially applying linear parallel rows of staggered staples through compressed tissue.

BACKGROUND

Surgical stapling instruments used for substantially sequentially applying parallel, linear rows of staggered staples through compressed living tissue are well known in the art, and are commonly used for closure of tissue or organs prior to transection or resection, and for occlusion of organs in thoracic and abdominal plasty procedures. Surgical staplers of this type may be used during an open surgical procedure where an incision is made to provide access to the surgical site, or during a laparoscopic surgical procedure where tissue stapling is accomplished through a generally cylindrical access tube.

Surgical staplers which substantially sequentially fire staples typically comprise a staple housing for enclosing the staples prior to their formation, a pusher having a cam surface, and staple drivers substantially adjacent each staple. As used herein, when it is said that a surgical stapler "substantially sequentially" fires the staples in a linear row, it is meant that the stapler completes the application of some staples in a row before the application of other staples in the row, as opposed to a stapler which generally simultaneously fires all of the staples in a row. In a stapler which "generally simultaneously" fires staples, during at least a portion of the movement of its firing mechanism, all of the staples are in motion relative to the staple housing. The circular stapler disclosed in U.S. Pat. No. 4,754,909 generally simultaneously fires a circular array of staples, and the stapler described in EPO Application No. 514 139 to Solyntjes et al. generally simultaneously fires a plurality of linear, parallel rows of staggered staples.

In a stapler which substantially sequentially fires staples in a linear row, the firing mechanism typically comprises a pusher, staple drivers generally adjacent staples in a staple housing and an anvil. The pusher is movable relative to the staple housing in a firing direction. On its leading edge, the pusher has a camming surface situated at an acute, included angle with the firing direction. The staple drivers have cam follower surfaces for engaging the camming surface to move the staple drivers in a staple formation or staple driving direction which is typically perpendicular to the firing direction. Movement of the staple drivers in the staple formation direction ejects the staples from the staple housing and presses the ejected staples against specially shaped surfaces on the anvil to engage, form and close the staples in tissue between the staple housing and anvil.

In an unformed condition, staples used in a sequentially fired stapler typically comprise a backspan and a pair of legs projecting from the backspan that each include a sharp tissue penetrating surface. During formation of an individual staple, the tips first pass through tissue and then engage the specially shaped surface of the anvil. The force required to initially buckle or bend the staple legs when they engage the anvil is relatively greater than the force required to pierce tissue.

When properly formed, the staples assume a substantially "B" shaped configuration. Improperly or only partially formed staples may result in a variety of adverse consequences for a patient, such as inadequate hemostasis, excessive bleeding or a weakened staple line which could result in dehiscence of the anastomosis or leakage.

In the present context, the phrase, "formation force" pertains to the force required to apply a staple. The phrase "initial maximum formation force" refers to the initial maximum force encountered during formation of a staple which corresponds to the initial buckling or bending of the legs. During the formation of staple loops, a second maximum formation force is encountered that is also substantially greater than the force required to penetrate the tissue. The second maximum formation force may be greater than the initial maximum formation force. The second maximum formation force corresponds to the formation of the legs into loops after the buckling of the legs, but before the legs engage each other or the backspan, or before the final formation of the legs into loops.

It is also believed that a third maximum formation force may be encountered during the final formation of the staple. The third maximum formation force is believed to correspond to staple legs engaging either each other or the backspan, or to the increasing bending forces encountered by the buckling of the staple legs on an ever shortening effective beam length. The third maximum formation force is also relatively greater than the maximum force required to pierce tissue. Graphs of the firing force versus pusher displacement are found in U.S. Pat. Nos. 3,494,533 and 4,767,044, but these graphs do not illustrate the third maximum formation force that was discovered by applicants and mentioned above.

FIG. 42 is a graph of the formation force curve in pounds versus the pusher stroke in inches for a prior art titanium staple which was slightly overcrimped in simulated thin tissue. The staple was a staple designed generally for use in a stapler as shown in EPO Application No. 514 139 to Solyntjes et al. Each of the first, second and third maximum formation forces are referenced as #1, #2 and #3.

The prior art is replete with mechanisms designed to reduce the overall formation force experienced by the surgeon in firing all of the rows of staples in the stapler. For example, U.S. Pat. No. 3,499,591 illustrates a stapler with pusher devices staggered so that peak forces for staples are not simultaneously encountered. European Patent Application No. 545029 discloses further attempts to reduce the operative effort.

A general analysis of the relationship between the pusher, pusher driver and anvil reveals that by reducing the angle between the camming surface of the pusher and the firing direction (or conversely, increasing the angle between the camming surface of the pusher and the staple driving direction), the force encountered by the surgeon may be reduced. U.S. Pat. Nos. 3,079,606 to Bobrov et al. and 3,315,863 to O'Dea illustrate sequentially fired staplers with pushers having camming surfaces at small included angles with the firing direction. The illustrated angles appear to be less than about twenty (20) degrees.

A distal or nose portion for the staple housing is required to house the distal portion of the pusher while the proximal portion of the pusher completes the firing of the distalmost staple in a staple row. When the pusher camming surface forms a shallow angle with the firing direction, the distal or nose portion of the staple housing is relatively lengthy. Such staplers encounter problems when used in a surgical procedure which requires the stapler to staple tissue in a remote position which is not readily accessible to a surgeon, as such staplers require relatively lengthy distal end portions (or "noses") of the staple housing to accommodate the small angled pusher. Examples of such procedures include deep pelvic or thoracic cavity procedures where space is a limiting factor.

The distal end portion of a stapler may limit the access of the stapler to the tissue to be stapled. For example, tissue such as bone or adjacent blood vessels may prevent proper placement of such a stapler on tissue. A stapler with a lengthy distal end portion is also believed to be difficult to maneuver in cramped or tight spaces at least in part due to the lengthy distal end portion.

These problems are only exacerbated when the sequentially fired stapler comprises a laparoscopic stapler, as the surgeon's access to the tissue to be stapled is even further restricted due to the access tube. It is particularly important in laparoscopic surgery to provide a cartridge as small as possible in order to maximize the maneuvering room between the distal end of the access tube and the tissue to be stapled.

U.S. Pat. No. 4,596,351 to Fedotov et al. discloses a stapler having a pusher with a curvilinear camming surface. The angle between the curvilinear camming surface of the pusher of Fedotov et al. and the firing direction constantly changes rendering it difficult to accurately predict the effective angle encountered during the various stages of staple formation.

It is also noted that the pushers of the GIA-b 60 surgical stapler (generally available from U.S. Surgical Corporation) appear to comprise first and second linear camming surfaces, but do not include a third linear camming surface. This stapler is generally designed for use in laparoscopic surgery.

Other approaches to the problem of reducing the firing force encountered by a surgeon comprise surgical staplers that are manually fired but include a) a mechanism for providing a mechanical advantage, or b) a powered instrument which utilizes stored energy (such as gas stored in a cylinder). Staplers with mechanical advantage comprise the 3 cm Endostapler known as the Endo GIA-30, available from U.S. Surgical Corporation of Norwalk, Connecticut and the 6 cm Endostapler known as the Endopath Linear Cutter 60 available from Ethicon, Inc. of Somerville, N.J. However, these types of staplers are expensive to manufacture, complex and do not provide a surgeon with direct feedback as to how the position of the firing lever travel relates to the length of tissue that has been stapled (and optionally cut).

Another approach to the problem of reducing the firing force experienced by a surgeon is shown in U.S. Pat. Nos. 5,083,695 and 5,141,144 the entire contents of which are herein expressly incorporated by reference. FIG. 18 illustrates a problem overcome by these types of staplers. The stapler 5 illustrated in FIG. 18 comprises a stapler substantially as shown in U.S. Pat. No. 4,863,088. With that stapler 5, the surgeon must push with enough force to overcome not only the firing force of the staples and frictional drag of the pushers and drivers, but also the frictional side or binding load created by pressing on the knob 6 at a location spaced from the axis 4 of the firing rod 11. The binding load is shown in FIG. 18 as the moment $M_F$ and is described by the following equation:

$$M_F = F_F H$$

where:

$F_F$=firing force (pounds); and

H=off center height (the distance between the point where the force $F_F$ is applied on the knob 6 and the axis 4 in FIG. 18).

Notably, since the knob 6 is mounted on the side of the stapler 5, when a surgeon presses on the knob 6 in a convenient manner, a moment is created about the firing rod 11. If the moment is large enough, it may even cause the pushers to engage the staple housing increasing the friction encountered by the firing assembly of the device. Thus, it can be seen that the moment may increase the firing force encountered by a surgeon.

The staplers shown in U.S. Pat. Nos. 5,083,695 and 5,141,144 have a firing handle body capable of being fired by simultaneously pressing on both sides of a firing button. The firing button may be located on both sides of the stapler to assist in eliminating any appreciable moment $M_F$. However, in order to fire the stapler in this manner, surgeons will use both hands. The surgeon should also push equally on both sides of the firing button to avoid a resultant moment on the firing rod. Such a technique is inconvenient during a laparoscopic surgical procedure where typically only one of the surgeon's hands is available for firing the stapler.

Another firing force issue arises when the surgical stapler is designed to apply six parallel rows of staples as opposed to the typical stapler which applies only four rows of staples. For example, in laparoscopic surgery where hemostasis and air leakage of lung tissue are particularly important, it may be desirable to add the fifth and sixth rows of staples.

FIG. 16 schematically illustrates a prior art, six row staple pattern applied by the laparoscopic GIA stapler available from U.S. Surgical of Norwalk, Conn. However, if substantially parallel pushers are used to apply that arrangement of staples, first 2, then 4, then 2, then 4 staples are applied. This may lead to a "chatter" problem or a "bumpy" feel to the instrument as peak firing forces fluctuate considerably. Assuming the pushers of the stapler are not staggered, it also requires the surgeon to exert a formation force sufficient to simultaneously form four staples.

DISCLOSURE OF THE INVENTION

The present invention provides a surgical stapler instrument for applying linear parallel rows of staples through compressed living tissue. The surgical stapler comprises a handle portion having surfaces adapted to be manually grasped by a surgeon; a cartridge retention portion and an anvil retention portion. An approximation means mounts the cartridge and anvil retention portions for relative movement between a closed position in which the anvil and cartridge retention portions are in closely spaced relationship for clamping tissue to be stapled therebetween and an open position in which the anvil and cartridge retention portions are spaced farther from each other than in the closed position. The anvil retention portion includes an anvil with a plurality of specially shaped surfaces.

The cartridge retention portion has a staple housing for enclosing a plurality of staples in substantially parallel, linear rows. Each of the staples have a backspan and a pair of legs projecting from the backspan. The legs buckle during formation of the staples into their desired "B" shape. The staple housing has staple drivers adjacent staples. The cartridge retention portion includes a plurality of pushers each having at least three linear camming surfaces. The pushers may comprise a portion of the staple housing or alternatively the stapler itself.

The staple housing has a plurality of longitudinally extending pusher slots for receiving the pushers to afford movement of the pushers in a firing direction between pre-fired and fired positions, and a plurality of driver channels for receiving the staple drivers to afford movement of the staple drivers in a staple driving direction between pre-eject and ejected positions.

Each of the staple drivers has a cam follower surface for engaging the linear camming surfaces of a pusher to move the staple driver from the pre-eject toward the ejected position to substantially sequentially eject the staples from the staple housing and press the ejected staples against the specially shaped surfaces of the anvil to engage, form and close staples in tissue clamped between the staple housing and the anvil.

According to one aspect of the present invention, the three linear camming surfaces of the pushers comprise a) a first camming surface for engaging a staple driver during initial tissue penetration of a staple; b) a second camming surface for engaging a staple driver during initial buckling of the legs of a staple; and c) a third camming surface for engaging a staple driver after the legs of a staple have been initially buckled and during the closing of the staple in tissue. The first camming surface forms a first included angle with the staple driving direction. The second camming surface forms a second included angle with the staple driving direction that is greater than the first included angle. The third camming surface forms a third included angle with the staple driving direction that is different than the first and second included angles.

According to another aspect of the present invention, the proximal portion of a stapler comprises first and second sides, top and bottom portions, a firing handle channel extending between the sides to define a space between the top and bottom portions, and finger engagement surfaces that are sized and shaped to be engaged by the fingers of a stapler firing hand of a surgeon. The stapler further includes a firing handle mounted in the firing handle channel for movement in the firing direction between pre-fired and fired positions. The firing handle has digit engagement surfaces dimensioned and shaped to be receive a digit such as the thumb of the firing hand of a surgeon.

The firing handle channel is sized and shaped to afford passage of at least one digit of the surgeon's hand from one of the first and second sides, through the space, to the other of the first and second sides to afford manual grasping of the firing handle. This feature of the stapler provides an ambidextrous quality in that the stapler is conveniently fired by both left and right handed surgeons.

The stapler includes a firing rod between the firing handle and the pushers. The firing rod has proximal and distal portions for transmitting a firing force from the firing handle to the pushers to move the pushers in the firing direction. The proximal portion of the firing rod defines a proximal portion firing axis substantially parallel to the firing direction.

The firing handle and proximal portion of the firing rod are constructed and arranged to afford transmission of a force directly along the proximal portion firing axis so that the proximal portion of the firing rod may remain substantially free of a moment caused by the surgeon pressing on the firing handle to move the firing handle from the pre-fired toward the fired position.

The features of the staplers described above may be utilized in any stapler which fires a plurality of parallel rows (2, 3, 4, 5 etc.) of staples in compressed tissue. According to another aspect of the present invention, the stapler comprises the cartridge retention portion having a staple housing for enclosing six rows of staples in substantially parallel, linear rows. The six rows are spaced laterally across the staple housing such that any line drawn laterally across the staple line crosses at least three staples.

In another embodiment of a six row surgical stapler, the stapler comprises the cartridge retention portion having a staple housing for enclosing six adjacent rows of staples in substantially parallel, linear rows. The distance between adjacent staples in the same row defines a staple pitch. In this embodiment the six rows are spaced such that each row is longitudinally offset from all of the other rows. Preferably, the staples in each of the rows are longitudinally offset at least ⅙ of the pitch P from any staple in any of the other rows. More preferably, one of the rows is longitudinally offset ⅓ of the pitch from each of the adjacent rows.

In another aspect of a surgical stapler for firing six parallel rows of staples in compressed tissue, the stapler comprises six rows of staples that are separated into a first set of three parallel linear rows and a second set of three parallel linear rows by a centerline or knife travel line. Each of the three parallel linear rows of staples in the first set are spaced such that it is longitudinally offset from the other two rows of staples in the first set. Similarly, each of the three parallel linear rows of staples in the second set are spaced such that it is longitudinally offset from the other two rows of staples in the second set. Preferably, in this embodiment, at least one of the rows of staples in the first set is longitudinally aligned with one of the rows of staples in the second set. More preferably, the first set of rows is a mirror image of the second set of rows.

Yet another aspect of the present invention comprises a surgical stapler having a firing means movable in a firing direction between pre-fired and fired positions to substantially sequentially eject the staples in a row from the staple housing and press the ejected staples against the specially shaped surfaces of the anvil to engage, form and close staples in tissue clamped between the staple housing and the anvil. The stapler includes a firing handle and a firing rod operatively associated with the firing means for movement between the pre-fired and fired positions, and an optional knife for cutting tissue. The stapler has a means that is operatively associated with the firing means and mounts the knife for movement between a pre-fired position in which the knife is located in the proximal portion of the staple housing and a fired position in which the knife is located in the distal portion of the staple housing. The stapler includes a novel trapping means for trapping the knife in the distal end portion of the staple housing in the fired position and for restricting return movement of the knife from the fired toward the pre-fired position once the firing means has been moved from the pre-fired to the fired position. Preferably, the trapping means includes an interference member for physically blocking return movement of the pushers from the fired to the pre-fired position.

Preferably, the firing means comprises: a) staple drivers adjacent staples, and a plurality of pushers each having a camming surface, b) the staple housing having a plurality of longitudinally extending pusher slots adapted to receive the pushers to afford movement of the pushers in the firing direction, and c) a plurality of driver channels for receiving the staple drivers to afford movement of the staple drivers in a staple driving direction between pre-eject and ejected positions. In this embodiment, the trapping means traps the pushers in the distal end portion of the staple housing.

As mentioned above, the trapping means comprises at least one of the pushers having a hook surface, the staple housing including a trap surface in substantially the distal end portion of the staple housing for receiving the hook surface of the pusher when the pusher is in the fired position, and biasing means for biasing the pusher vertically away from the tissue to be stapled so that the hook surface of the pusher is biased toward the trap surface of the housing.

Optionally, the stapler may include means mounting the knife for vertical movement between an extended position with the knife projecting vertically beyond the tissue engagement surface of the staple housing and a retracted position with the knife spaced farther from the anvil than in the extended position. In this embodiment, the knife includes a bearing surface, the staple housing has a guide channel having a cutting motion portion for receiving the bearing surface of the knife as the knife moves between the pre-fired and fired positions, and the guide channel has an abutment portion situated approximately perpendicular to the cutting motion portion of the guide channel for abutting the bearing surface of the knife to restrict longitudinal movement of the knife from the fired toward the pre-fired position. Biasing means are present for vertically biasing the knife from the extended toward the retracted position.

In another preferred embodiment, the stapler includes a one-way coupling between the firing rod, pushers and knife which affords reciprocal movement of portions of the firing rod between pre-fired and fired positions but which only affords movement of the pushers and knife from the pre-fired toward the fired position. This embodiment provides a tactile indication to a surgeon that the stapler has been fired as the resistance to movement of the firing assembly is different for fired and unfired staple housings.

The features of the present invention may be utilized in surgical staplers used in either open or laparoscopic surgical procedures. Some of the aspects of the present invention are particularly useful in staplers utilized in laparoscopic surgical procedures.

BRIEF DESCRIPTION OF THE DRAWING

The present invention will be further described with reference to the accompanying drawing wherein like reference numerals refer to like parts in the several views, and wherein:

FIGS. 13 through 15 sequentially illustrate the operation of a firing mechanism of a stapler according to the present invention wherein:

FIG. 13 is a side view of a firing mechanism of a stapler according to the present invention illustrating the positions of a pusher, staple driver and staple as the staple initially pierces tissue;

FIG. 14 is a side view of a firing mechanism of a stapler according to the present invention illustrating the positions of a pusher, staple driver and staple as the legs of the staple begin to buckle;

FIG. 15 is a side view of a firing mechanism of a stapler according to the present invention illustrating the positions of a pusher, staple driver and staple as the loops of the staple are forming;

FIG. 16 is a schematic view of portions of six parallel rows of staples in a pattern created by a prior art stapler or optionally a stapler according to the present invention;

FIG. 17 is a schematic view of portions of six parallel rows of staples in a pattern created by a stapler according to the present invention;

FIGS. 22 through 27 are side views of the stapler of FIG. 21 and sequentially illustrate the positions of a pusher and knife during the firing of the stapler wherein:

FIG. 22 illustrates the pusher and knife in a pre-fired position;

FIG. 23 illustrates the pusher slightly advanced during an initial portion of the firing stroke and the knife in the same longitudinal position as shown in FIG. 22;

FIG. 24 illustrates the pusher and knife after they have been advanced a significant portion of the firing stroke;

FIG. 25 illustrates the knife and pusher as they have been advanced slightly more distally than in FIG. 24 with the knife beginning to descend vertically toward the pusher along an abutment surface;

FIG. 26 illustrates the pusher advanced slightly beyond its position in FIG. 25 and the knife descended toward the bottom of the abutment surface;

FIG. 27 illustrates the pusher and knife after they have been advanced to a distalmost position and after a lockout device has been actuated;

FIGS. 28 through 35 are side views of another embodiment of a stapler according to the present invention and sequentially illustrate the positions of a pusher and knife during the firing of the stapler wherein:

FIG. 28 illustrates the pusher and knife in a pre-fired position;

FIG. 29 illustrates the pusher slightly advanced during an initial portion of the firing stroke and the knife after it has vertically ascended a ramp surface on the staple housing;

FIG. 30 illustrates the pusher and knife after they have been advanced a significant portion of the firing stroke;

FIG. 31 illustrates the knife and pusher as they have been advanced slightly more distally than in FIG. 30 with the knife beginning to descend vertically toward the pusher along an abutment surface;

FIG. 32 illustrates the pusher advanced slightly beyond its position in FIG. 31 and the knife descended toward the bottom of the abutment surface;

FIG. 33 illustrates the pusher and knife after they have been advanced to a distalmost position and after a lockout device has been actuated;

FIG. 34 is a schematic illustration of portions of a second embodiment of staple rows according to the present invention which simulates a top view with the staples rotated about ninety degrees about their backspans and with the spacing between the rows exaggerated to illustrate details;

FIG. 35 is a schematic view of portions of a third embodiment of staple rows according to the present invention which illustrates six parallel rows of staples in a pattern;

FIG. 37 is a schematic side view of an optional firing rod and knife assembly according to the present invention;

FIG. 38 is a schematic illustration of the assembly of FIG. 37 taken approximately at detail 38—38 of FIG. 37 which illustrates the direction of movement of the assembly during firing and retraction strokes with arrows;

DETAILED DESCRIPTION

Figure 1:
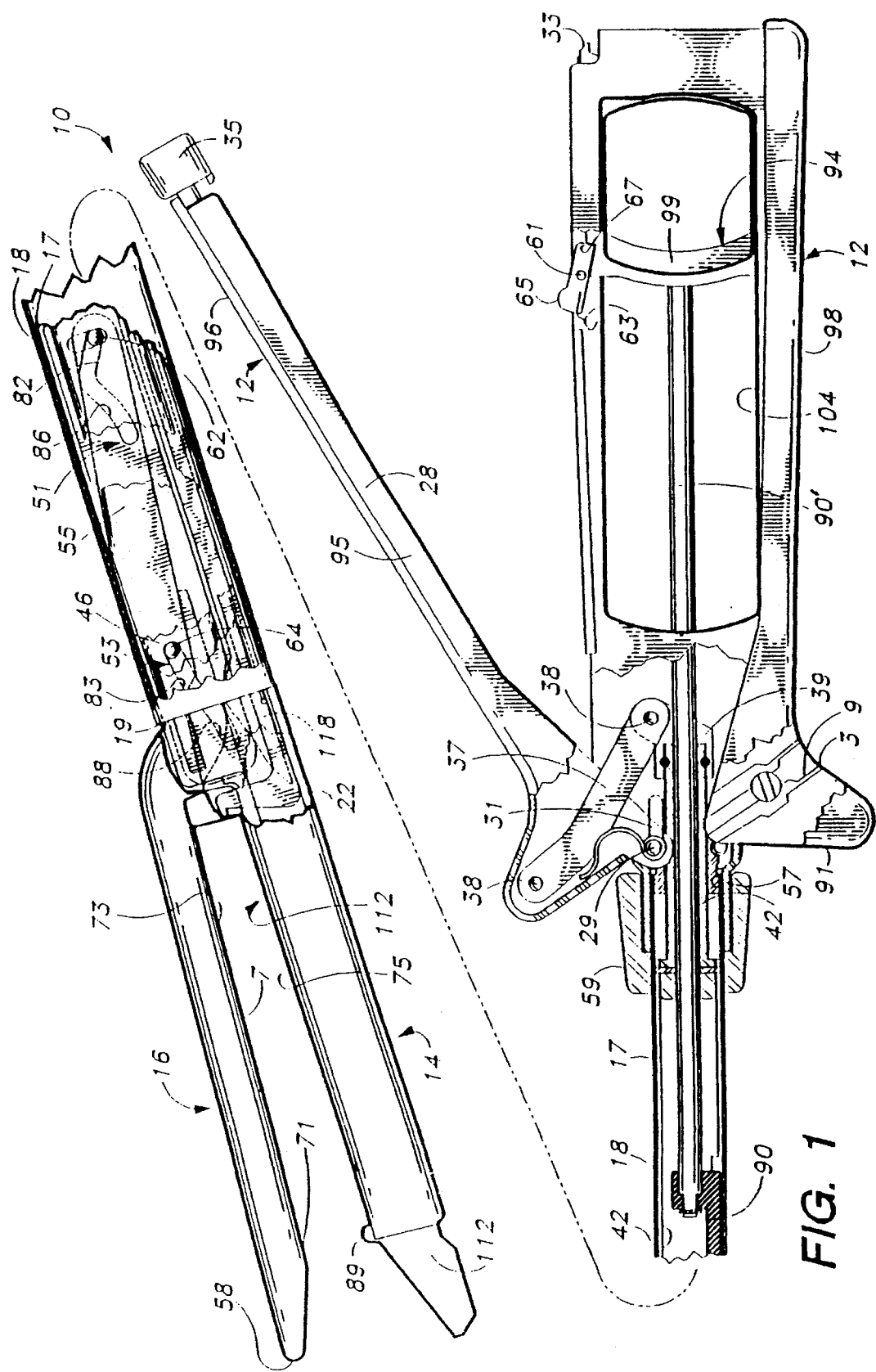
FIG. 1 is a side view of a first embodiment of surgical stapling instrument according the present invention showing the cartridge and anvil of the stapler in an open position, with middle portions of the stapler omitted to emphasize details of proximal and distal portions of the stapler, and with the distal portion of the stapler enlarged relative to the proximal portion to illustrate details of the distal portion.

Referring now to FIGS. 1 through 5 of the drawing, there is shown a first embodiment of surgical stapling instrument according to the present invention, generally designated by reference numeral 10. The surgical stapler 10 is designed to apply staples to compressed tissue, preferably during a laparoscopic surgical procedure.

The stapler 10 may comprise a single use disposable stapler, a reusable surgical stapler or a reloadable disposable surgical stapler. As used in this application, the phrase "reusable surgical stapler" means a surgical stapler which may not only be fired several times on the same patient (with, for example, the use of replaceable cartridges or staple housings), but may also be sterilized and reused on a different patient. Such a stapler stands in opposition to what is known in the art as a "disposable surgical stapler". While a reloadable disposable surgical stapler may be reused several times on the same patient, a disposable surgical stapler is not meant to be sterilized or used on a plurality of patients. A single use disposable stapler is designed to be used (fired) once and disposed after that single use.

In general, the stapler 10 comprises a proximal portion including a handle portion having surfaces 12 adapted to be manually grasped by a surgeon, and a distal portion including a cartridge retention portion 14 and an anvil retention portion 16.

The anvil retention portion 16 comprises an anvil having specially shaped surfaces 7 (best seen in FIGS. 13–15) the function of which will be described in greater detail below. The anvil may comprise a permanent anvil or a replaceable anvil. As used in this application, the phrase "replaceable anvil" means an anvil which may be removed from the stapler by medical personnel, and then replaced with a different, sterilized or refurbished anvil. A permanent anvil is fixedly attached to an anvil retention portion of the stapler and is not designed to be replaced during the life of the stapler. An anvil is described in published Canadian Patent application No. 1,284,551 and Australian patent document No. 589,001 (the contents of each of which are herein incorporated by reference). The anvil may be constructed from, for example, a medical grade stainless steel.

Between the proximal and distal portions, the stapler 10 has a housing 17 having exterior surface 18 terminating in distal end 19. The exterior surface 18 is preferably substantially cylindrical and is sized and shaped to engage the interior surfaces of an access tube of a trocar assembly. The housing 17 is elongate and defines a longitudinal axis L (see FIG. 3A) for the stapler 10.

Preferably, the housing 17 is rotatable about the longitudinal axis L of the stapler 10 relative to the proximal portion of the stapler. A collar 59 and bearing sleeve 57 allow the housing 17 to rotate relative to the proximal portion of the stapler 10. The collar 59 may have exterior surfaces such as ribs for enhancing the manual grasping of the collar by a surgeon.

When the stapler 10 is used during a laparoscopic surgical procedure, the distal portion of the stapler 10 is threaded through the interior surfaces of the access tube of a trocar (such as the trocar in U.S. Pat. No. 5,152,754, the entire contents incorporated by reference). Preferably, the access tube engagement surface 18 is dimensioned (sized and shaped) to engage or abut the interior surfaces of the access tube (not shown) of a trocar to restrict leakage of fluid from the abdominal cavity of a patient. Preferably the access tube engagement surface 18 is cylindrical with an outer diameter slightly less than the inner diameter of the access tube.

The stapler 10 has an approximation means for mounting the cartridge and anvil retention portions 14 and 16 for relative movement between: (1) a closed position (FIG. 3) in which the cartridge and anvil retention portions are in closely spaced relationship for clamping tissue to be stapled therebetween and (2) an open position (FIG. 1) in which the cartridge and anvil retention portions 14 and 16 are spaced farther from each other than in the closed position. In the open position, tissue to be stapled may be received between the cartridge and anvil retention portions 14 and 16.

Figure 4:
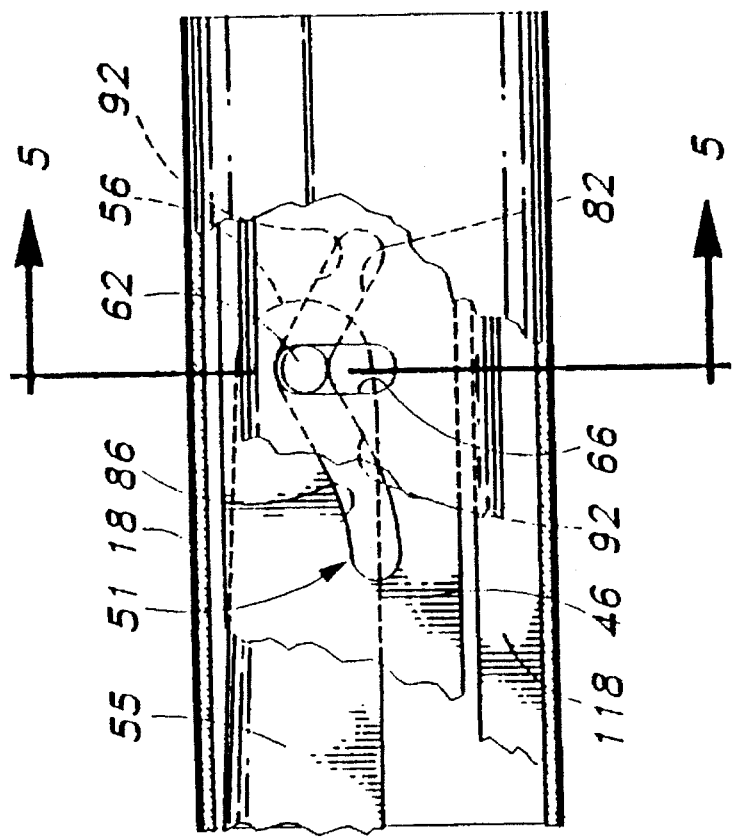
FIG. 4 is an enlarged detailed view of the stapler of FIG. 2 taken generally at the circled portion of FIG. 2.
Figure 5:
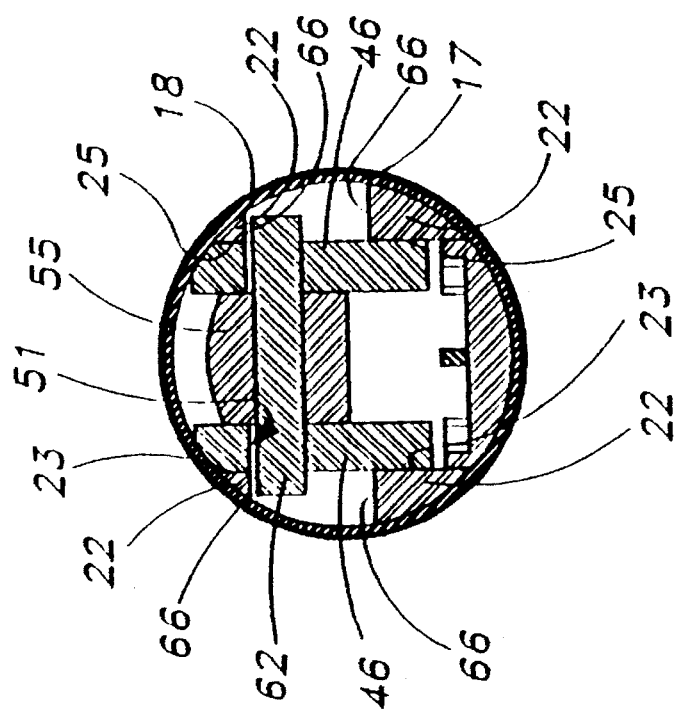
FIG. 5 is a sectional view of the stapler of FIG. 4 taken approximately along lines 5—5 of FIG. 4.

Generally, the approximation means comprises three assemblies which are best seen in FIGS. 4 and 5. The first assembly comprises a cartridge frame 22. The cartridge frame 22 preferably has a U-shaped channel adapted to closely receive exterior surfaces of a staple housing 112 so that the stapler 10 may comprise a reusable or reloadable disposable stapler.

As discussed above, the housing 17 is rotatable about the longitudinal axis of the stapler 10 relative to the proximal portion of the stapler 10. However, the cartridge frame 22 is mounted on the stapler so that the cartridge frame 22 does not move longitudinally or rotate relative to the housing 17. The cartridge frame 22 has opposite first and second side bearing surfaces 23 and 25 which are laterally spaced about the longitudinal axis of the stapler 10 (see FIG. 5A).

Figure 3:
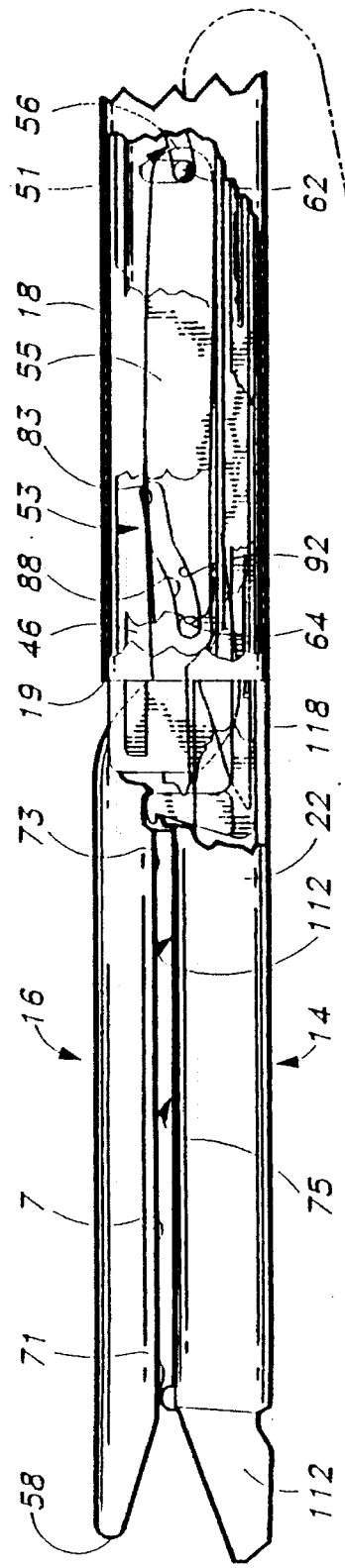
FIG. 3 is a side view of the surgical stapling instrument of FIG. 1 showing the cartridge and anvil of the stapler in a closed position, and with the distal portion of the stapler enlarged relative to the proximal portion to emphasize details of the distal portion.
Figure 3:
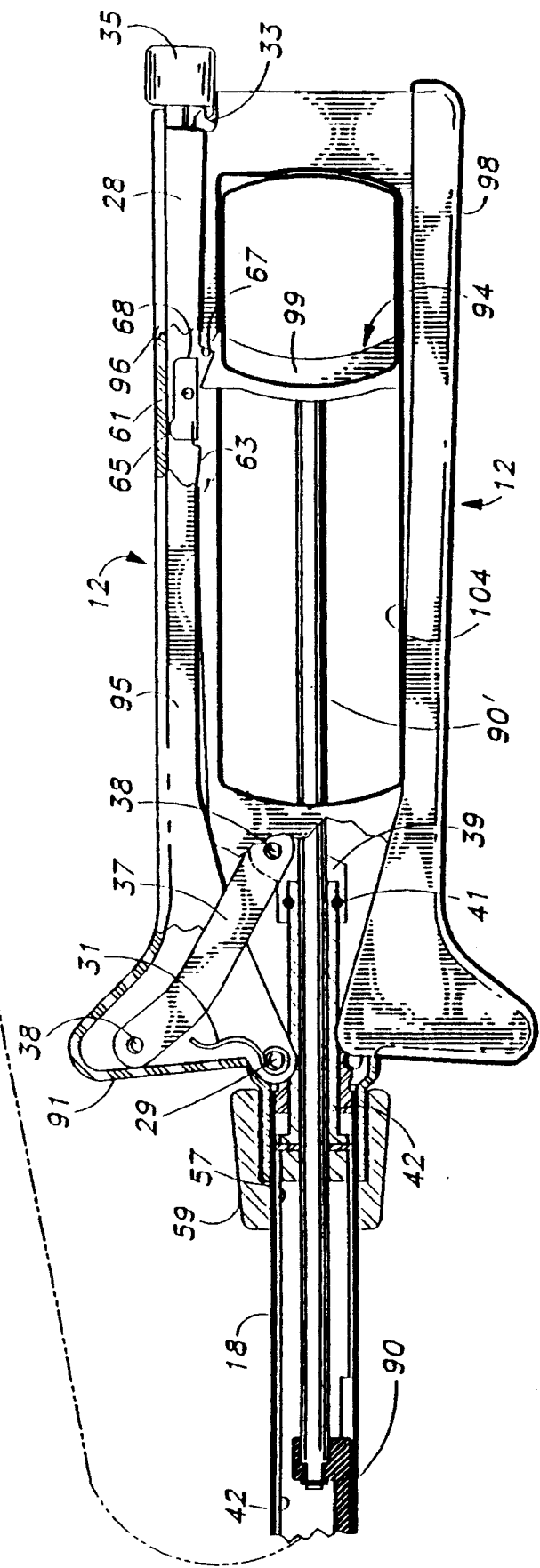

The second assembly of the approximation means comprises a longitudinally movable assembly. The longitudinally movable assembly is operatively associated with a locking lever 28 that is movable between an open (FIG. 1) and a closed position (FIG. 3). Pin 29 mounts the locking lever 28 for pivotal movement relative to the housing 17 about the pin 29. Optionally, the distal portion of the locking lever 28 may be designed to slightly interfere with the collar 59 when the locking lever 28 is in the closed position so that, when the locking lever 28 is in the closed position, the interference resists rotation of the housing 17 relative to the proximal portion.

Torsion spring 31 biases the locking lever 28 toward the open position. Latch 33 engages retention surfaces on release lever 35 to secure the locking lever 28 in the closed position against the bias of spring 31. To open the stapler 10, a surgeon moves the release lever 35 laterally relative to the locking lever 28 to release the latch 33.

Linkage 37 and pins 38 translate the pivotal movement of the locking lever 28 into longitudinal, axial movement of collar 39 (Compare FIGS. 1 and 3). Bearing ring 41 connects the collar 39 to a control shaft 42 so that the collar 39 does not move longitudinally relative to the control shaft 42. The control shaft 42 and collar 39 are axially reciprocable within and relative to the housing 17. However, bearing ring 41 does afford rotational movement of the collar 39 relative to the control shaft 42 when the proximal portion of the stapler is rotated relative to the housing 17.

Figure 5A:
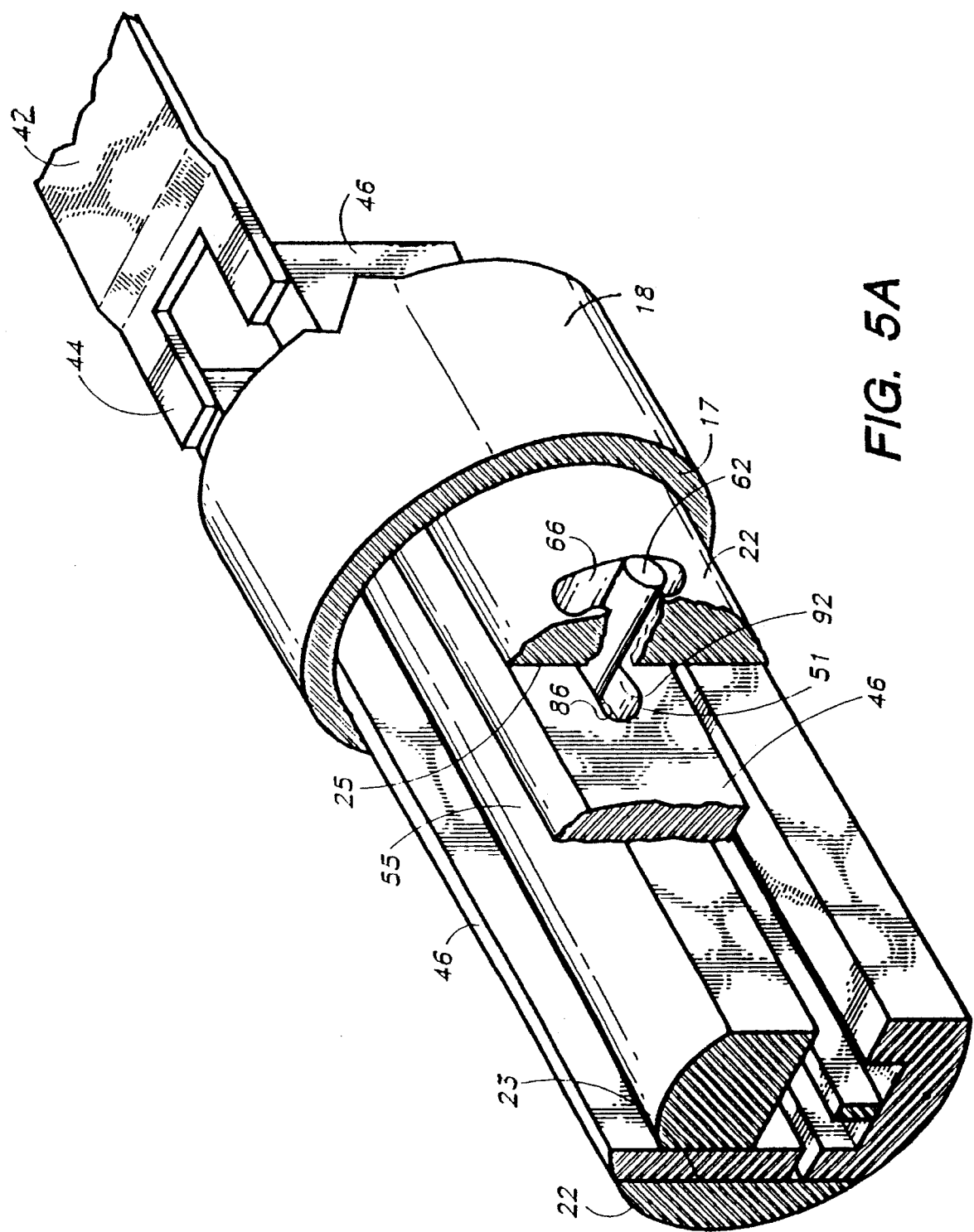
FIG. 5A is an enlarged perspective view of portions of the stapler of FIG. 1 which illustrates a clevis.
Figure 6:
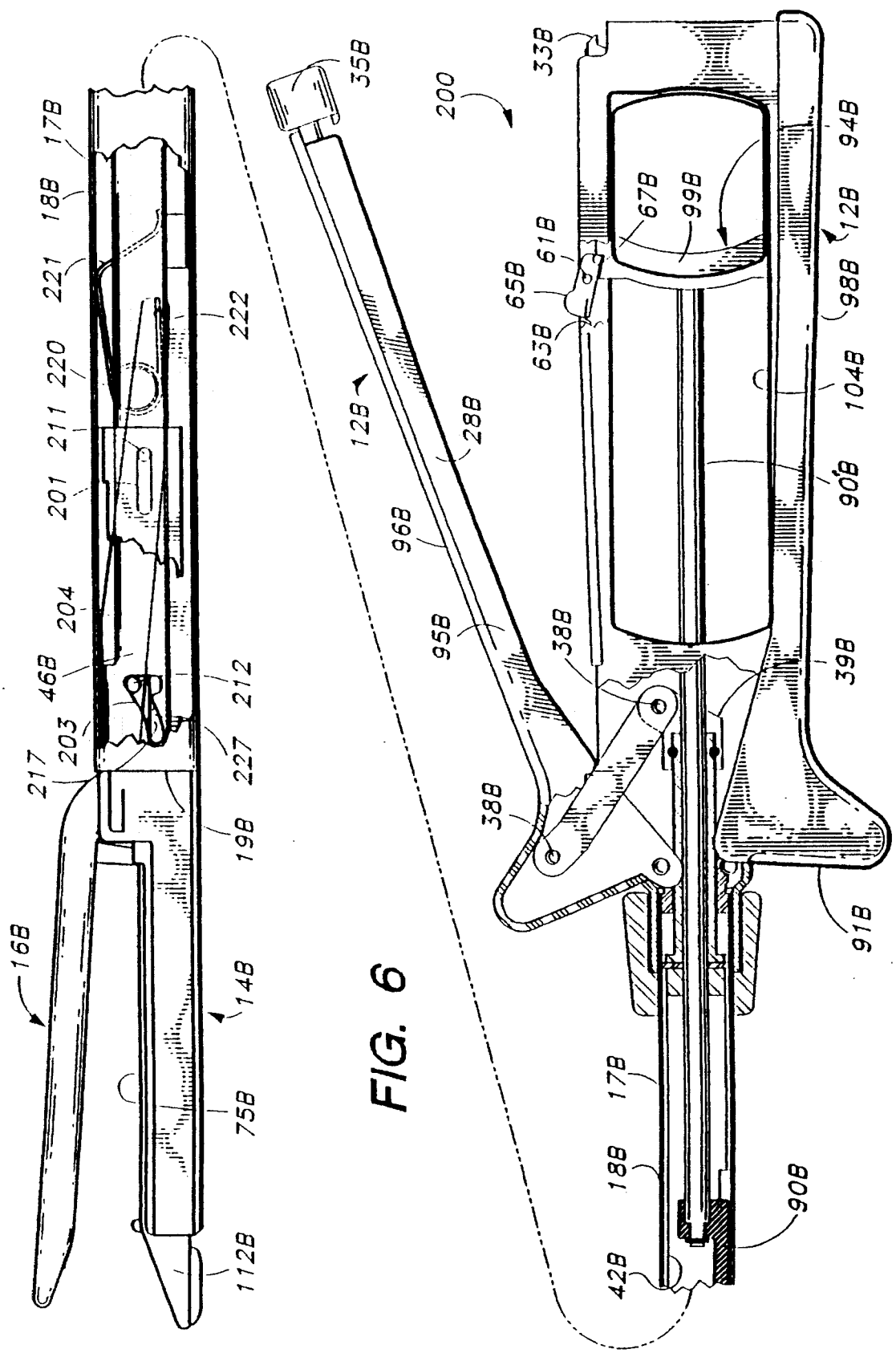
FIG. 6 is a side view of a second embodiment of surgical stapling instrument according the present invention showing cartridge and anvil portions of the stapler in an open position and with middle portions of the stapler omitted to emphasize details of proximal and distal portions of the stapler and with the distal portion of the stapler enlarged relative to the proximal portion in order to emphasize details.

As best seen in FIG. 5A, U-shaped clevis 44 fixedly attaches a pair of transversely spaced guide members 46 (FIGS. 4 and 5) to the control shaft 42 so that the guide members 46 do not move relative to the control shaft 42. The first and second bearing surfaces 23 and 25 of the cartridge frame 22 receive and abut their respective guide members 46 and assist in constraining the guide members 46 to substantially axial longitudinal movement relative to the cartridge frame 22.

The guide members 46 each have a first, proximal control groove 51 and a second, distal control groove 53, the operation of which will be described in greater detail below. To close the stapler 10, the control shaft 42 is moved proximally from the position in FIG. 1 to the position in FIG. 3 substantially linearly and parallel to the axis of the stapler 10. Reversing the direction of the control shaft 42 (e.g. distal movement of the shaft 42) opens the stapler 10.

The third assembly of the approximation means of the stapler 10 comprises an anvil assembly which includes the anvil retention portion 16. The anvil assembly includes a proximal portion 55 sandwiched between the guide members 46 and terminating in proximal end 56. The anvil also has distal end 58. Proximal post 62 and fulcrum post or axle 64 are fixedly attached to and project laterally or transversely (relative to the longitudinal axis of the stapler 10) from spaced positions on the proximal portion 55 of the anvil assembly.

The fulcrum post or axle 64 is sized and shaped to be received in the distal control grooves 53 of the guide members 46. The fulcrum post 64 affords substantially seesaw motion of the anvil assembly relative to the distal control grooves 53 of the guide members 46.

As best seen in FIGS. 4 and 5, the proximal post 62 projects through the proximal control grooves 51 of the guide members 46 and is sized and shaped to be received in limiter slots 66 of the cartridge frame 22. Unlike the fulcrum post 64 which only projects sufficiently laterally to be received in the control grooves 53, the proximal post 62 projects laterally into opposite anvil limiter slots 66 in the cartridge frame 22. The limiter slots 66 are generally perpendicular to the longitudinal axis of the stapler 10 which limits the longitudinal movement of the anvil relative to the housing 17 (and cartridge frame 22). The limiter slots 66 do, however, afford movement of the proximal post 62 in a direction generally perpendicular to the longitudinal axis (vertically in FIGS. 1–5) so that the anvil may substantially seesaw about fulcrum post 64 relative to second control groove 53.

Figure 2:
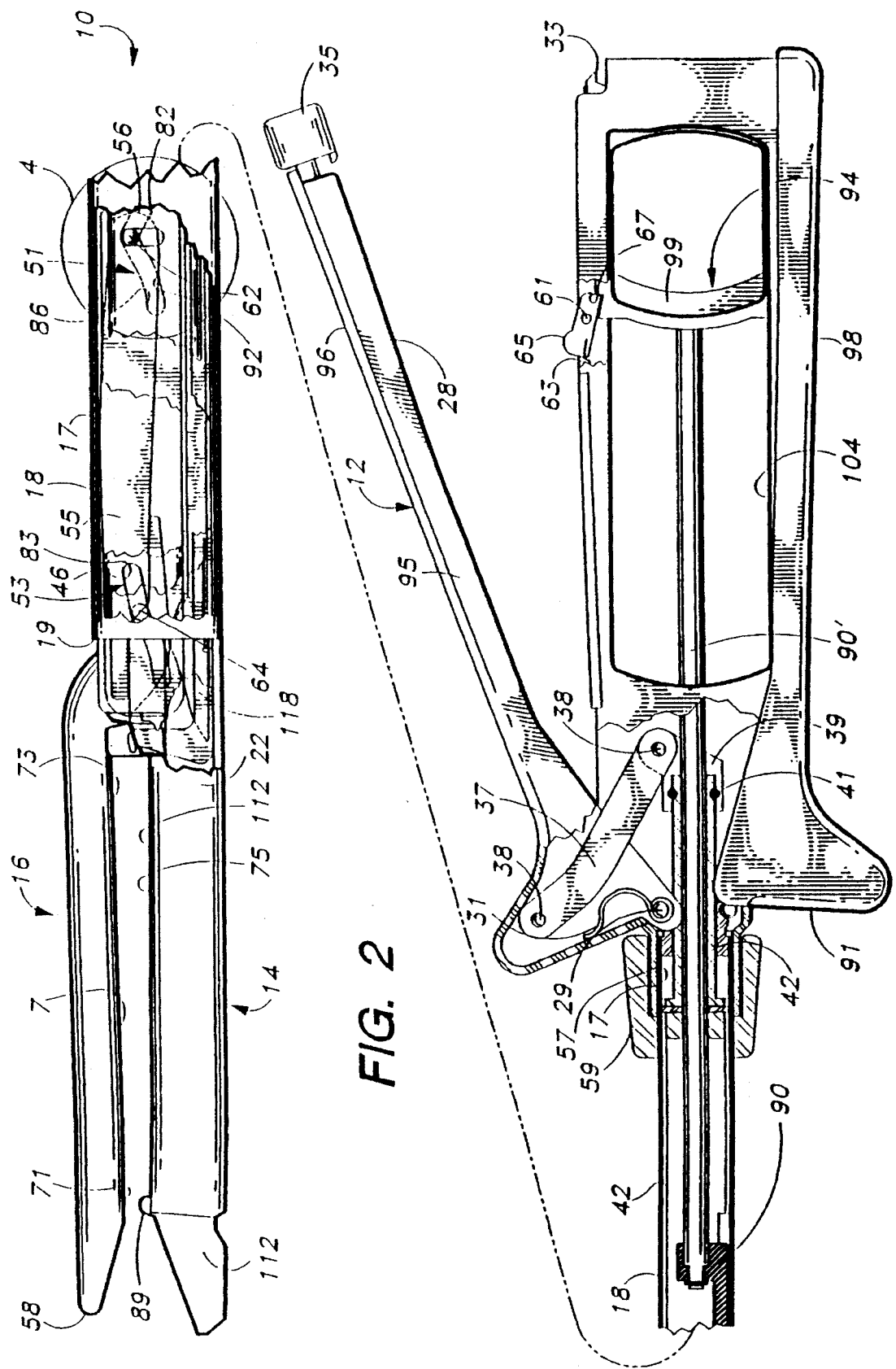
FIG. 2 is a side view of the surgical stapling instrument of FIG. 1 showing the cartridge and anvil of the stapler in a partially closed position, and with the distal portion of the stapler enlarged relative to the proximal portion to emphasize details of the distal portion.

The shapes of the first and second control grooves 51 and 53 are important to control the motion of the anvil retention portion 16 as it moves from an open position (FIG. 1) to a partially closed position (FIG. 2) and finally to a closed position (FIG. 3). FIGS. 1 through 3 show preferred embodiments of those shapes. For purposes of this discussion of the preferred embodiment, the anvil may be divided into a leading portion 71 and a trailing portion 73, and the positions of the locking lever 28 may be described as sequentially proceeding from an open position (FIG. 1) to a partially closed position (FIG. 2) and then to a closed position (FIG. 3).

During the movement of the locking lever 28 from the open to the partially closed position, the proximal post 62 is moved by leading edge closure portion 82 of first control groove 51 from a vertically lower position (FIG. 1) toward a vertically higher position (FIG. 2) in the limiter slot 66. The leading edge closure portion 82 causes the anvil to substantially seesaw about the fulcrum post 64 as the fulcrum post 64 is moved by an initial surface 83 of second control groove 53. The substantial seesaw movement of the anvil allows the leading portion 71 of the anvil to move toward the closed position more rapidly than the trailing portion 73.

Referring now to FIGS. 2 and 3, during movement of the locking lever 28 from the partially closed position to the closed position, the proximal post 62 is moved by trailing edge closure portion 86 of first control groove 51 from the vertical higher position (FIG. 2) to a vertical lower position (FIG. 3) in the limiter slot 66. At approximately the same time, the fulcrum post 64 is moved by a final motion surface 88 of second control groove 53. During the movement of the locking lever 28 from the partial closed position to the closed position, the trailing portion 73 of the anvil closes more rapidly than the proximal portion 71. In the preferred embodiment shown, the anvil substantially pivots about anvil stop 89 during the movement of the lever lock 28 from the partial closed position to the closed position. This motion resists extrusion of tissue from between the cartridge retention and anvil portions 14 and 16 and out the distal end of the stapler 10 to beneficially ensure that tissue remains clamped between the cartridge retention and anvil portions 14 and 16.

The first and second control slots 51 and 53 also include opening surfaces 92 for positively moving the anvil from the closed toward the open position. These surfaces allow a surgeon to positively exert force on the anvil to move it toward the open position by moving the locking lever 28 from the closed to the open position, as opposed, for example to a system that relies solely on the bias of a spring to open the stapler. This feature also avoids binding of the anvil and cartridge portions in the closed position when the stapler 10 is used to staple thick or resilient tissue. Optionally, this feature allows the surgeon to use the stapler as an active tissue dissector.

The movement of anvil from the open position (FIG. 1) toward the closed position (FIG. 3) is referred to as "tip to tail" closure as initially the leading portion 71 of the anvil moves toward the closed position more rapidly than the trailing portion 73, and then the relative speeds of closure of the leading and trailing portions 71 and 73 are reversed. Preferably, the leading portion 71 reaches a fully closed position prior to the trailing portion 73. This motion is believed to provide desirable clinical results as the initial closure of the distal portion resists extrusion of tissue from between the cartridge retention and anvil portions of the stapler.

The stapler 10 also includes means for holding and firing a plurality of staples. The firing means comprises means for sequentially firing a plurality of staples in a plurality of linear rows. Optionally, the stapler 10 may include a blade or knife 110 for cutting tissue between applied rows of staples. Once the approximation means is closed, the firing means is used to eject, form and close the staples in tissue. An example of a firing means for the stapler 10 may be seen in FIGS. 1–5, 13–15 and 21–27.

Figure 34:
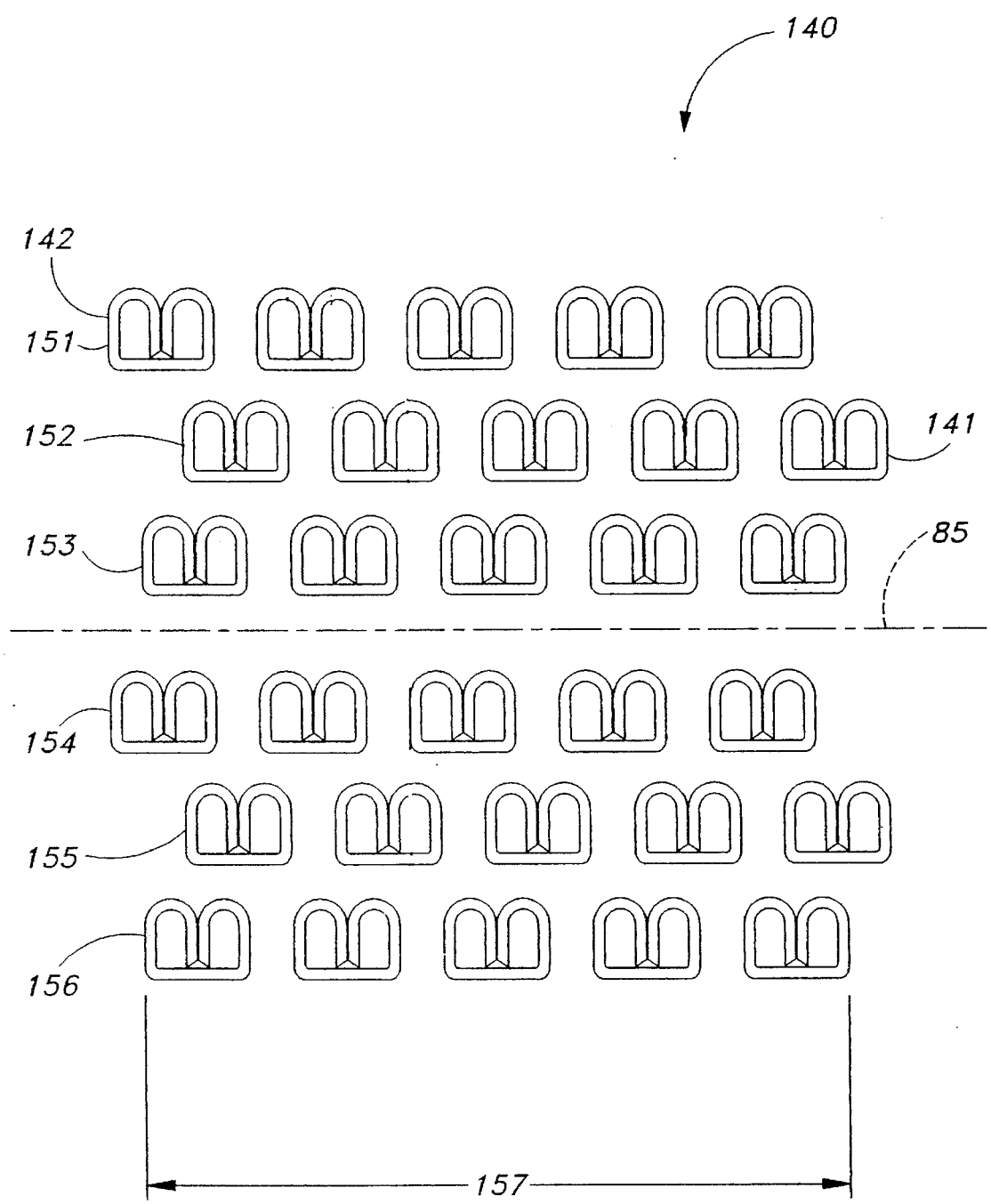

The cartridge retention portion 14 of the stapler 10 has a staple housing 112 for enclosing a plurality of staples 114 in substantially parallel, linear rows (FIGS. 16, 17 and 34). Typically, the staple housing 112 is removable from the cartridge retention portion 14 and replaceable with a replacement staple housing 112 rendering the stapler 10 a reusable or reloadable disposable stapler. The staple housing 112 may be replaced with a different staple housing so that the stapler 10 may be refired. This may be accomplished by including a detent and detent groove assembly (not shown) on the staple housing 112 and the cartridge frame 22, and optionally bifurcating the firing assembly which is described in greater detail below.

A staple 114 has a backspan 115 and a pair of legs 116 projecting from the backspan 115. As discussed in greater detail above, the legs are buckled during formation of the staples 114. As an example not intended to be limiting, the staple 114 may include a wire diameter of 9.8 or 9.4 mils, and may be construced from a material such as titanium.

The staple housing 112 also includes a plurality of staple drivers 120 situated adjacent staples 114. The stapler 10 also includes a plurality of pushers 118 each having at least three linear camming surfaces 1, 2 and 3. The pushers 118 may be reusable and integral with a firing rod 90 as would be recognized by one of ordinary skill in the art. Alternatively, the pushers 118 may be replaced with each different staple housing 112 in a manner discussed below with reference to FIGS. 37–38.

Figure 9:
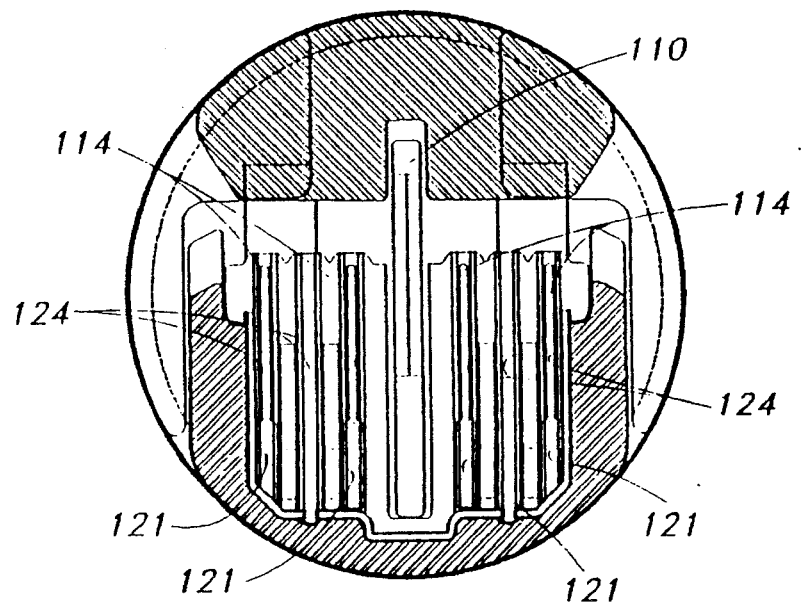
FIG. 9 is a sectional view of the stapler of FIG. 7 taken approximately along lines 9—9 of FIG. 7.
Figure 10:
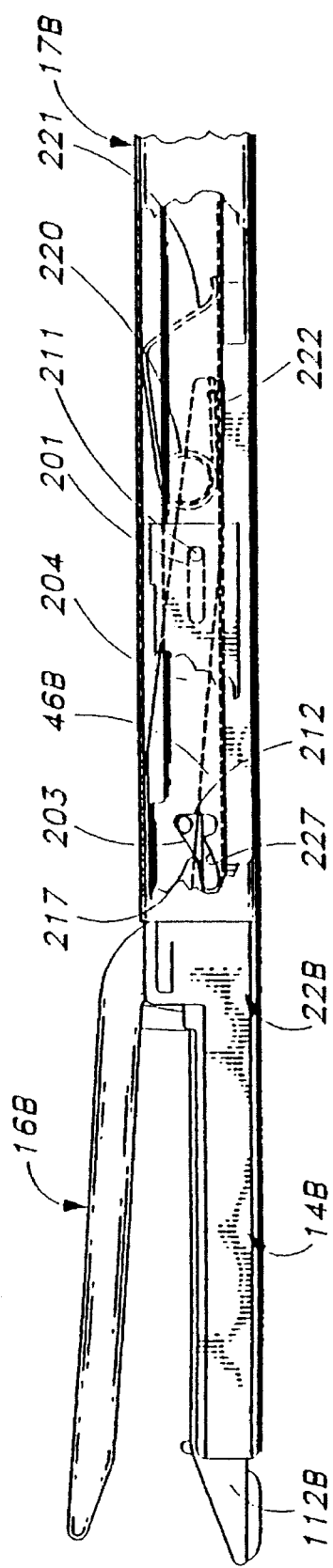
FIG. 10 is an enlarged side view of a distal portion of the stapler of FIG. 6.

Reference is now made to FIG. 9 with the understanding that, although FIG. 9 is a cross-section of the stapler shown in FIGS. 6–12, the cross section is similar to a cross-section that may be taken on the stapler shown in FIGS. 1–5. The staple housing 112 has a plurality of longitudinally extending pusher slots 121 adapted to receive the pushers 118 to afford movement of the pushers in a firing direction (the direction of the arrow 119 in FIGS. 13–15) between pre-fired (FIG. 21) and fired (FIG. 27) positions. The staple housing 112 has a plurality of driver channels 124 for receiving the staple drivers 120 to afford movement of the staple drivers 120 in a staple driving direction (the direction of the arrow 126 in FIGS. 13–15) between pre-eject (FIG. 13) and ejected (FIG. 15) positions.

Each of the staple drivers 120 have a cam follower surface 122 for engaging the linear camming surfaces 1, 2 and 3 of pusher 118 to move the staple driver 120 from the pre-eject toward the ejected position to substantially sequentially eject the staples 114 from the staple housing 112 and press the ejected staples 114 against the specially shaped surfaces 7 of the anvil to engage, form and close staples 114 in tissue 8 (FIGS. 13–15) clamped between the staple housing 112 and the anvil.

The first camming surface 1 forms a first included angle $\theta_1$ with the staple driving direction 126. The second camming surface 2 forms a second included angle $\theta_2$ with the staple driving direction 126 that is greater than the first included angle $\theta_1$. The third camming surface 3 forms a third included angle $\theta_3$ with the staple driving direction 126 that is different than the first and second included angles $\theta_1$ and $\theta_2$. The included angles (theta 1, 2 and 3; $\theta_1$, $\theta_2$ and $\theta_3$) that the linear camming surfaces 1, 2 and 3 form with the staple driving direction 126 operate to reduce the amount of longitudinal projection of the staple housing 112 beyond the distalmost staple 114 in a row and to reduce the firing force encountered by a surgeon. The angles (theta 1, 2 and 3; $\theta_1$, $\theta_2$ and $\theta_3$) also operate to reduce the amount that the stapler projects beyond the distal end 19 of the housing 17.

Figure 13:
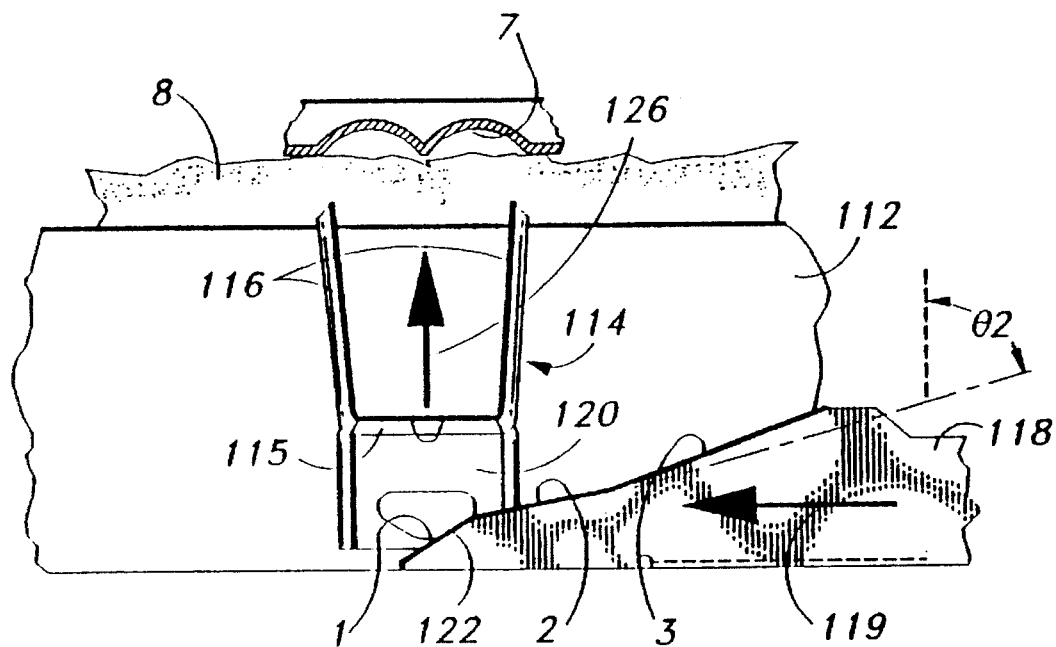
Figure 14:
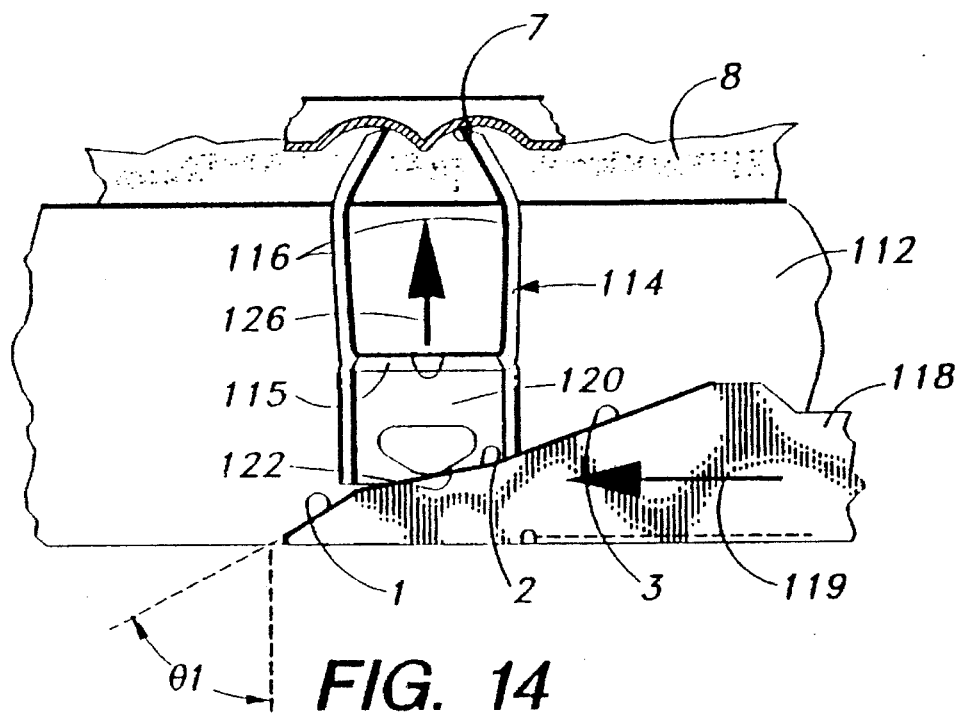
Figure 18:
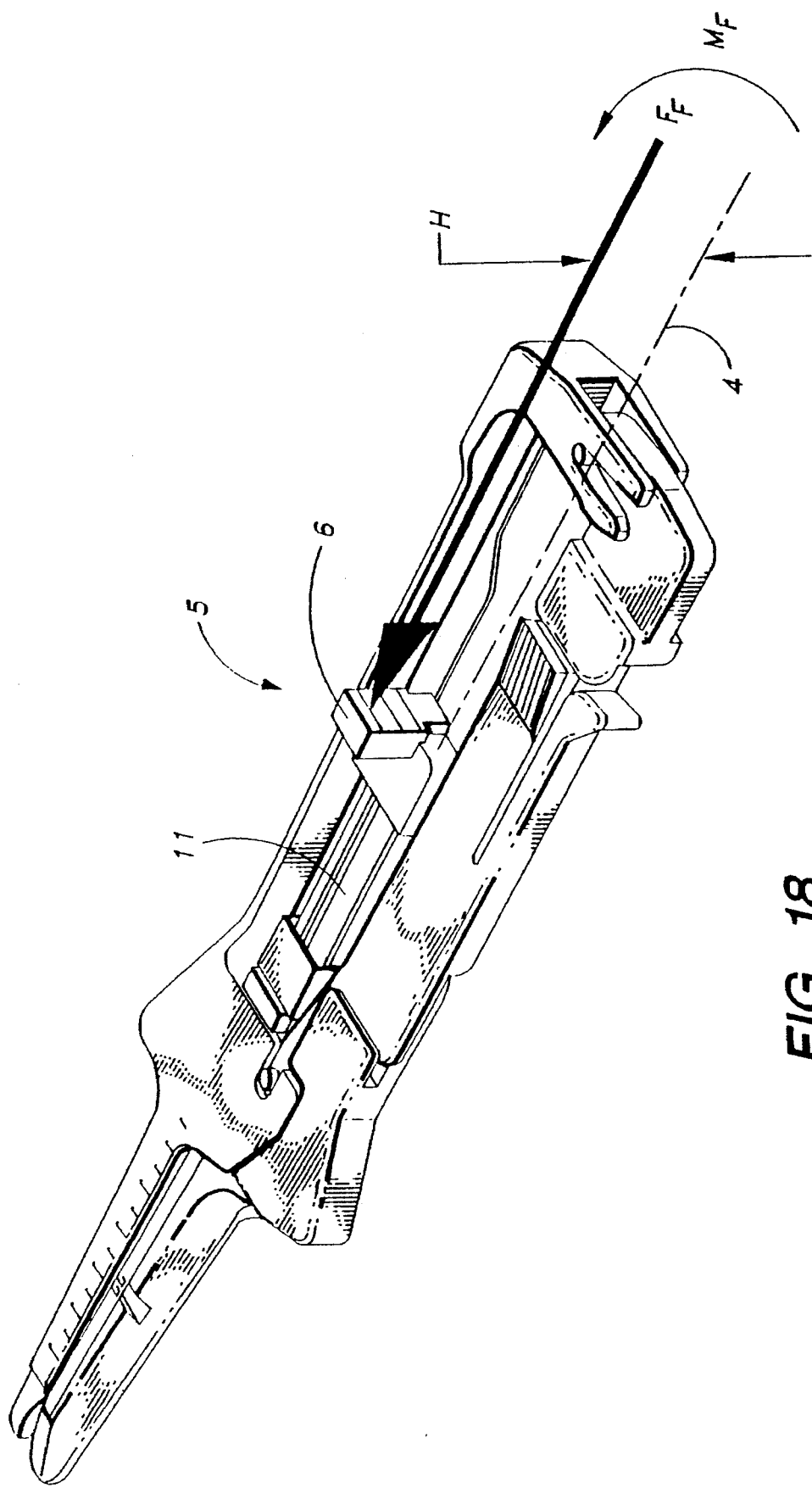
FIG. 18 is a perspective view of a prior art surgical stapler which illustrates a moment created about the firing rod.

FIGS. 13 through 15 sequentially illustrate the forming and closing of staple 114 in tissue 8. With reference to FIG. 13, the positions of the pusher 118, staple driver 120 and staple 114 are shown when the staple 114 is initially piercing tissue 8. At this point, movement of the pusher 118 in the firing direction 119 is translated into movement of the staple driver 120 in the staple driving direction 126 by engagement between the first camming surface 1 and the cam follower surface 122. The force required to pierce the tissue 8 is small relative to the forces encountered later in the staple forming operation. Thus, the angle $\theta_1$ may be relatively small in order to reduce the overall length of the pusher 118 and staple housing 112.

Preferably, the first included angle $\theta_1$ is between about forty-five (45) degrees and about sixty (60) degrees. More preferably, the first included angle is about sixty (60) degrees to reduce the overall length of the staple housing 112.

FIG. 14 illustrates the positions of a pusher 118, staple driver 120 and staple 114 just as the legs 116 of the staple 114 engage the specially shaped surfaces 7 of the anvil and begin to buckle. At this point, movement of the pusher 118 in the firing direction 119 is being translated into movement of the staple driver 120 in the staple driving direction 126 by the interaction of the second camming surface 2 and the cam follower surface 122. As discussed above, an initial maximum formation force is encountered at approximately this point. As a result, the angle $\theta_2$ is greater than the angle $\theta_1$ to reduce the overall resultant firing force experienced by the surgeon. The angle $\theta_2$ is preferably between about seventy-three (73) degrees and about seventy-eight (78) degrees. It should be noted that a linear camming surface in this range provides a predictable engagement angle with the staple driver 120 during the time when the initial maximum formation force for a staple is encountered, as opposed to a curvilinear pusher where the effective engagement angle between the pusher and staple driver direction is constantly changing. More preferably $\theta_2$ is about seventy-five (75) degrees.

FIG. 15 illustrates the positions of the pusher 118, staple driver 120 and staple 114 as the distal ends of the legs 116 of the staple 114 are deformed along specially shaped surfaces 7 of the anvil and form loops. Generally, just after the legs 116 initially buckle, the formation force for an individual staple is reduced, but it is nevertheless greater than the force required to pierce tissue 8. A second maximum formation force is thereafter encountered as discussed in the background section of this document.

When the second maximum formation force of the staple 114 is encountered, movement of the pusher 118 in the firing direction 119 is translated into movement of the staple driver 120 in the staple driving direction 126 by the interaction of the third camming surface 3 and the cam follower surface 122. The angle $\theta_3$ is greater than the angle $\theta_1$ to reduce the overall firing force experienced by the surgeon, but is typically less than the angle $\theta_2$ so that the overall length of the staple housing 112 and pusher 118 may be reduced. The angle $\theta_3$ is preferably between about sixty-seven (67) degrees and about seventy-two (72) degrees. In a preferred embodiment, the angle $\theta_3$ is about sixty-nine (69) degrees.

Figure 42:
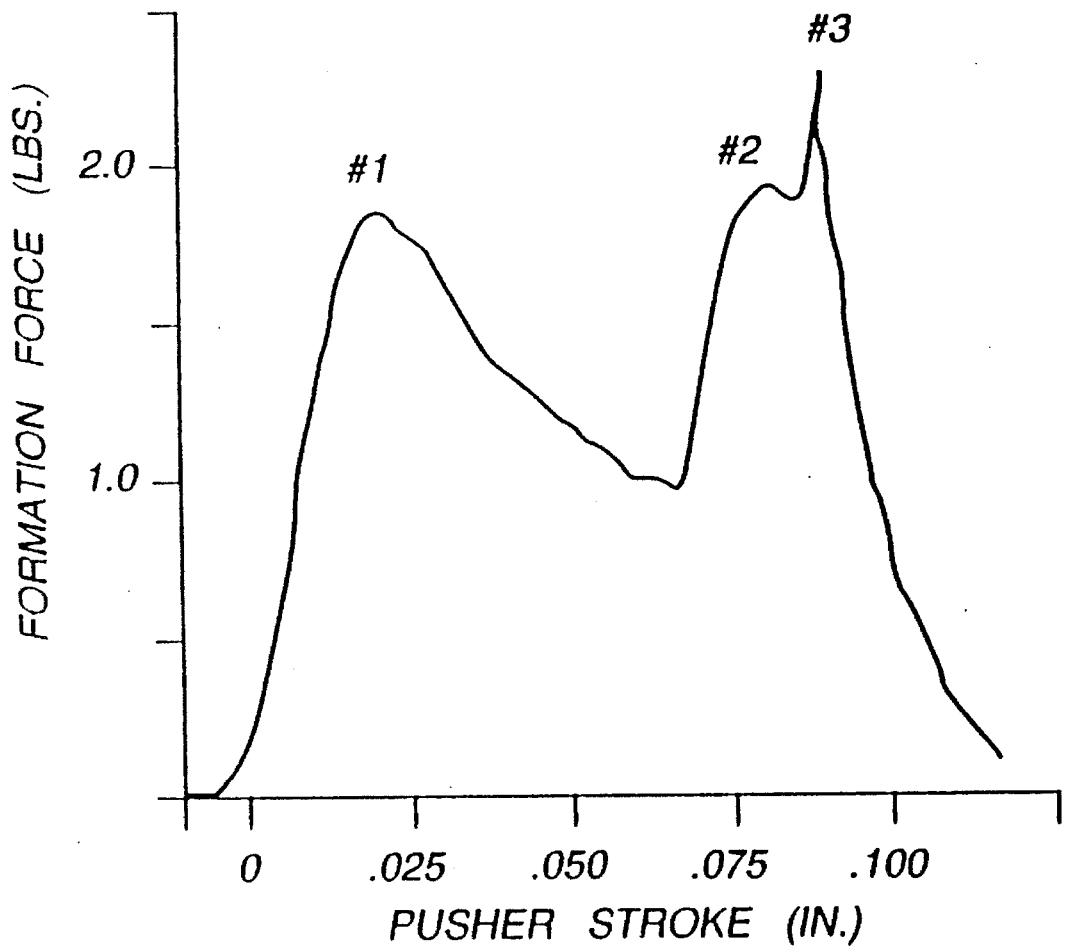
FIG. 42 is a firing force curve for an individual staple through simulated thin tissue, which illustrates first, second and third maximum formation force peaks.

From the above it can be seen that each linear surface 1, 2, 3 of the pusher 118 addresses a discrete portion of the staple formation curve (see FIG. 42). For example, the initial linear surface 1 corresponds to the initial tissue penetration of the staple, the linear surface 2 corresponds to the buckling of the staple legs and the third linear surface 3 corresponds to the terminal portion of the staple formation operation.

As discussed above, a third maximum formation force may be encountered subsequent to the positions of the elements shown in FIG. 15. Optionally, the pusher 118 may include a fourth linear camming surface (not shown) forming an angle $\theta_4$ (not shown) that is greater than the angle $\theta_3$ to accomodate the third maximum formation force.

Figure 19:
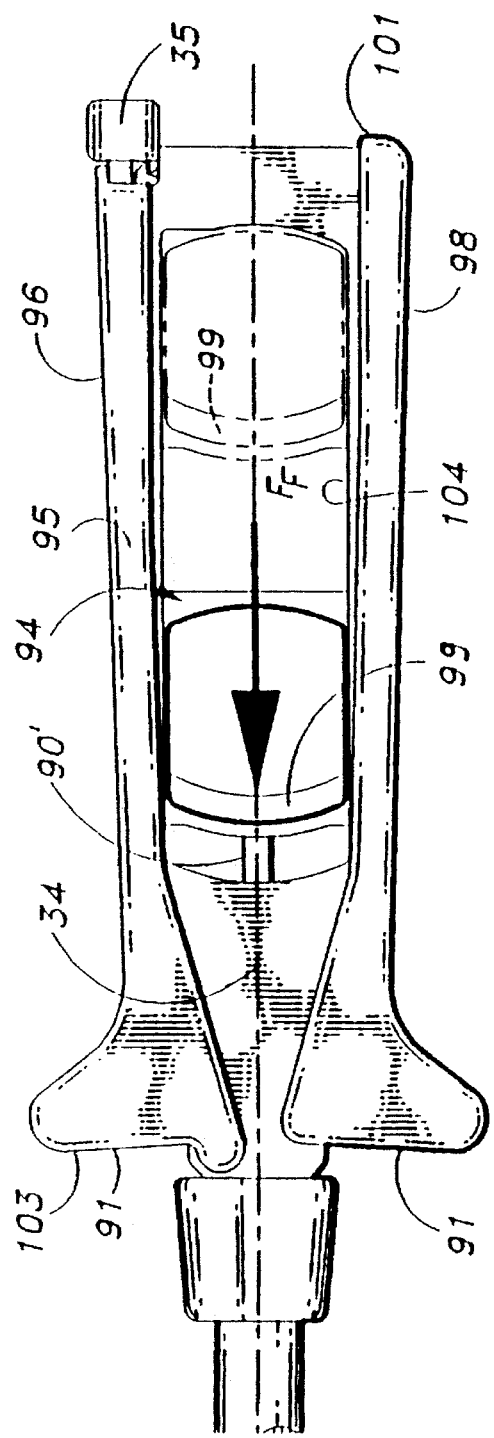
FIG. 19 is a side view of a surgical stapler according to the present invention which illustrates the position of a firing handle in a pre-fired position in hidden lines and in a fired position in solid lines.
Figure 20:
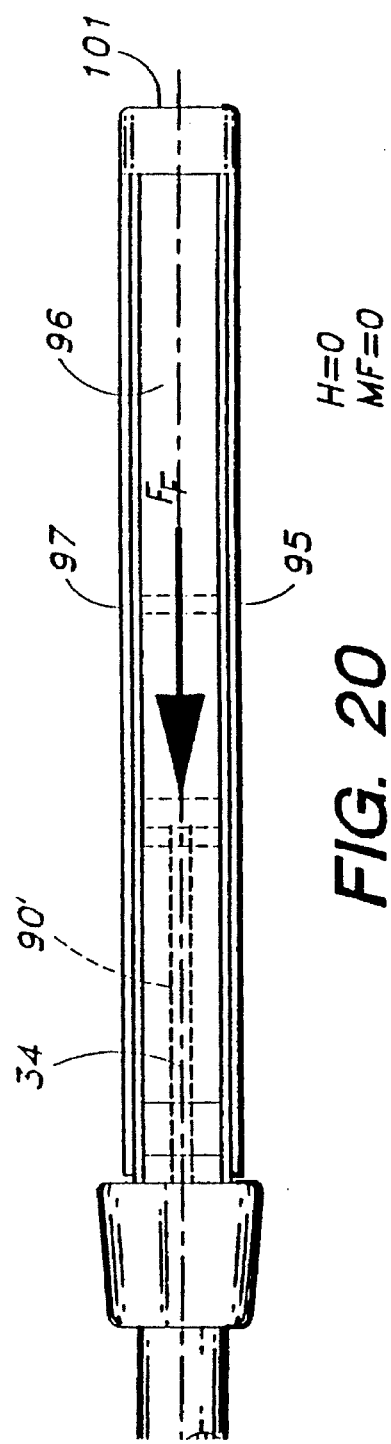
FIG. 20 is a top view of the surgical stapler of FIG. 19.

The firing assembly also includes a firing handle 94 designed to reduce the firing force encountered by the surgeon. Reference is now made to FIGS. 19 and 20 which schematically illustrates the location of the firing handle 94 on the stapler 10.

The proximal portion of the stapler 10 has first 95 and second 97 sides, top 96 and bottom 98 portions and proximal 101 and distal 103 ends. A firing handle channel 104 extends between the sides 95 and 97 and ends 101 and 103 to define a space between the top and bottom portions 96 and 98. At the distal end 103, the proximal portion of the stapler 10 has finger engagement surfaces 91 that are sized and shaped to be conveniently engaged by the fingers of a stapler firing hand of a surgeon.

The firing handle 94 is mounted in the firing handle channel 104 for movement in a firing direction between pre-fired (FIGS. 1, 2 and 3 and FIG. 19, dashed lines) and fired positions (FIG. 19, solid lines). The firing handle channel 104 is sized and shaped to afford passage of at least one digit of the surgeons's hand (such as the surgeon's thumb) from one of the sides 95 and 97 to the other of sides 95 and 97. The firing handle 94 has thumb engagement surfaces 99 dimensioned and shaped to receive the thumb of the firing hand of a surgeon so that the stapler 10 may be fired in a motion that is similar to the motion that may be used to eject fluid from a common syringe. The thumb engagement surfaces 99 are preferably designed so that the stapler 10 may be fired by either hand of a surgeon, thereby giving the firing assembly of the stapler 10 an ambidexterity.

The firing handle 94 is fixedly connected to a firing rod 90 that is situated between the firing handle 94 and the pushers 118. FIGS. 37 and 38 illustrate an optional one-way adapter 87 (described in greater detail below) that transmits the firing force from the firing rod 90 to the pushers 118. The optional one-way adapter affords placement of the pushers 118 in the staple housing 112 so that they may be replaced with different staple housings when the stapler is a reloadable disposable or a reusable stapler. The firing rod 90 transmits a firing force from the firing handle 94 to the pushers 118 to move the pushers 118 in the firing direction.

A proximal portion of the firing rod is illustrated in FIGS. 1–3 and 19–20 by reference character 90'. As best seen in FIG. 1, when the firing handle 94 is in the pre-fired position, at least a portion of the proximal portion of the firing rod 90' is located within the firing handle channel 104 and between the proximal and distal ends 101 and 103 of the proximal portion of the stapler. The proximal portion of the firing rod 90' defines a proximal portion firing axis 34 illustrated in FIGS. 19 and 20. The proximal portion firing axis 34 is substantially parallel to the firing direction 119. It may be seen in FIGS. 1–3 that the proximal portion of the firing rod 90' is rotationally connected to the rest of the firing rod 90 so that when the proximal portion of the stapler 10 is rotated relative to the housing 17, the proximal portion of the firing rod 90' may rotate relative to the rest of the firing rod 90.

As best seen in FIGS. 19 and 20, the firing handle 94 and proximal portion of the firing rod 90' are constructed and arranged to afford transmission of a force $F_F$ directly along the proximal portion firing axis 34. Since there is substantially no space between the point of application of the force $F_F$ (the position where the surgeon places his or her thumb) and the proximal portion firing axis 34, the proximal portion of the firing rod 90' remains substantially free of a moment caused by the surgeon pressing on the firing handle 94 to move the firing handle from the pre-fired (FIG. 19 dashed lines) to the fired position (FIG. 19 solid lines). This arrangement of structure reduces the frictional resistance of the firing assembly by a substantial amount and thus reduces the resultant force experienced by a surgeon.

The stapler 10 also includes a means for preventing the firing handle 94 from moving from the pre-fired position toward the fired position until the cartridge and anvil retention portions 14 and 16 are moved from the open toward the closed position. As best seen in FIGS. 1–3, the proximal portion of the stapler 10 includes a rocker arm pivotally mounted by pin 61 for movement between a) a blocking position (FIGS. 1 and 2) which restricts movement of the firing handle 94 from the pre-fired toward the fired position, and b) a free-movement position (FIG. 3) which affords movement of the firing handle 94 from the pre-fired toward the fired position. A leaf spring 63 biases the rocker arm toward the blocking position.

The firing handle 94 has notch surfaces 67 for receiving blocking surface 68 of the rocker arm when the rocker arm is in the blocking position. The rocker arm also includes lever lock abutment surface 65 for engaging surfaces on the locking lever 28 when the lever lock is in the closed position (FIG. 3). When the locking lever 28 moves from the partially closed position (FIG. 2) to the closed position (FIG. 3), surfaces on the locking lever 28 engage the lever lock abutment surface 65 on the rocker arm and cause the rocker arm to rotate counterclockwise in FIGS. 2 and 3 against the bias of spring 63 from the blocking to the free-movement position. The rocker arm restricts movement of the firing handle 94 from the pre-fired toward the fired position unless the cartridge retention and anvil retention portions are in the closed position.

Figure 3A:
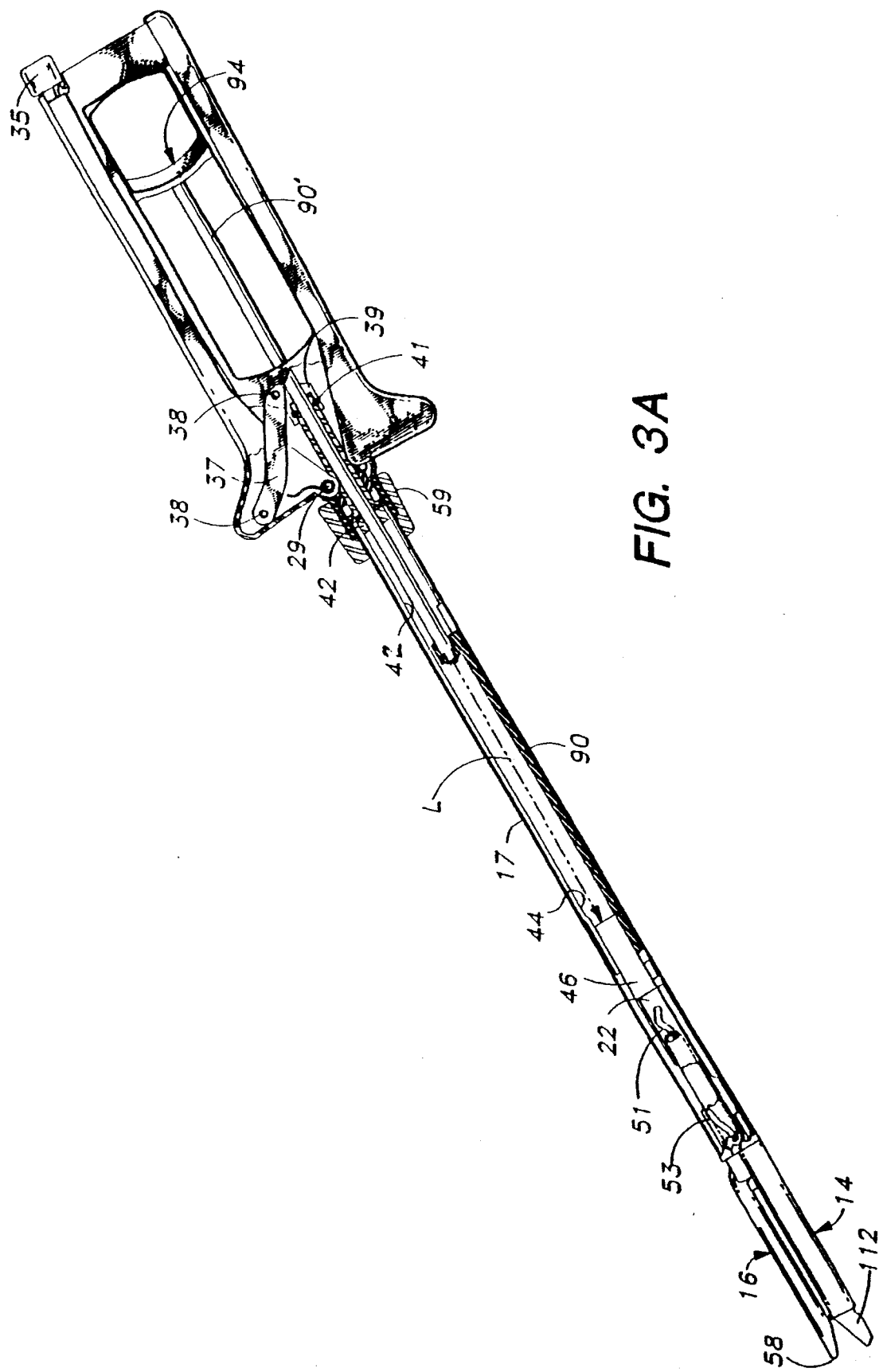
FIG. 3A is a side view of the surgical stapling instrument of FIGS. 1 through 3 which illustrates the proximal and distal ends at the same size.

Optionally, the stapler 10 may include the firing assembly depicted in FIGS. 21–27. The staple housing 112 depicted in FIGS. 21–27 is elongate to define a longitudinal axis substantially parallel to the axis L (FIG. 3A). The staple housing 112 has tissue engagement surface 75, and proximal 76 and distal 77 end portions. The staple housing 112 also has a plurality of longitudinally extending pusher slots 121 adapted to receive pushers 118 to afford movement of the pushers 118 in a firing direction between pre-fired (FIGS. 21 and 22) and fired (FIG. 27) positions, and a plurality of driver channels 124 for receiving the staple drivers 120 to afford movement of the staple drivers 120 in the staple driving direction 126 between pre-eject and ejected positions.

The firing rod 90 and firing handle 94 are operatively associated with the pushers 118 for movement between the pre-fired and fired positions. The stapler 10 optionally has a trapping means for trapping either the knife 110 or both the knife 110 and pushers 118 in the distal portion 77 (e.g. substantially adjacent the distal end of the staple housing 112) of the staple housing 112 in the fired position. The trapping means also prevents return movement of either the knife 110 or preferably both the knife 110 and pushers 118 from the fired (FIG. 27) toward the pre-fired (FIGS. 21 and 22) position once they have been moved from the pre-fired to the fired position. The trapping means physically blocks movement of either the knife 110 or both the knife 110 and pushers 118 from the fired toward the pre-fired position.

Figure 22:
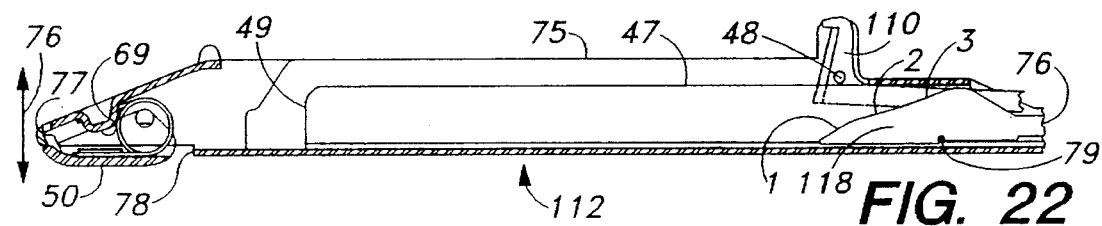
Figure 23:
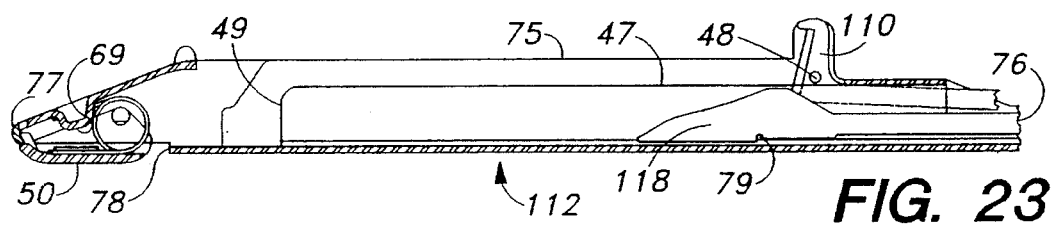
Figure 24:
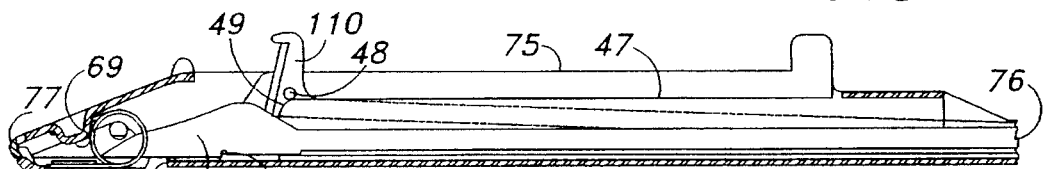
Figure 25:
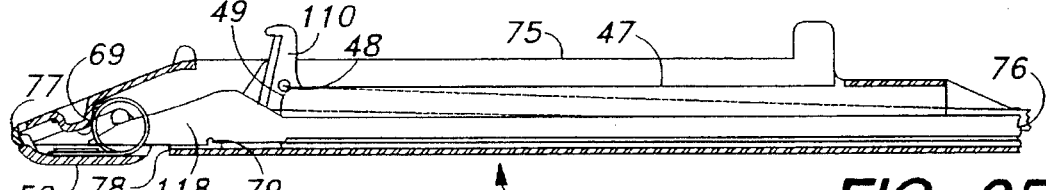
Figure 26:
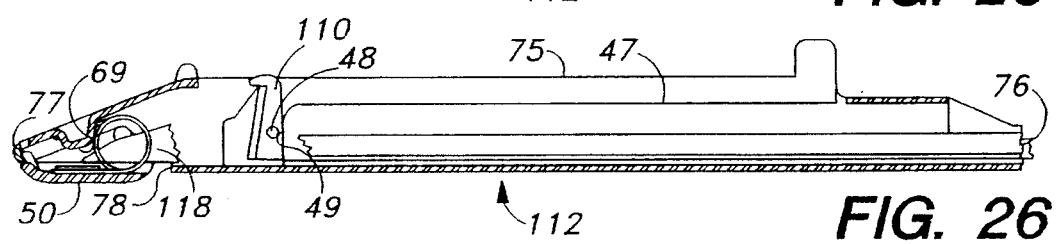
Figure 27:
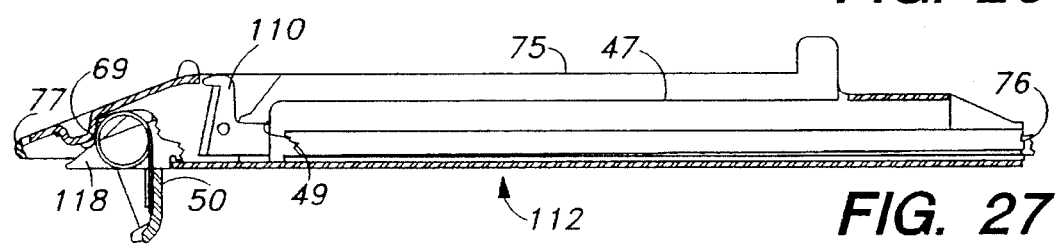
Figure 28:
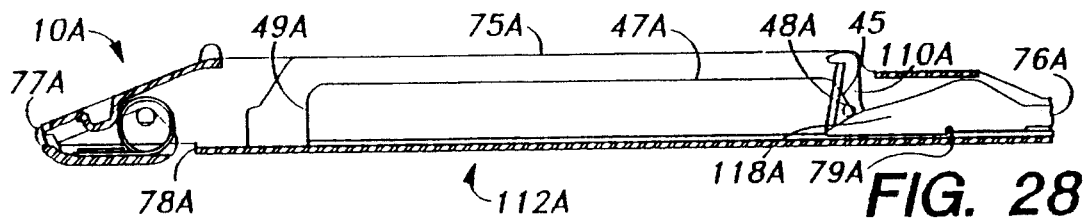
Figure 29:
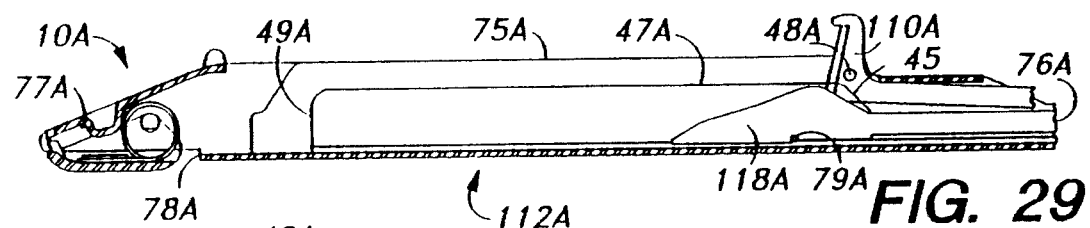
Figure 30:
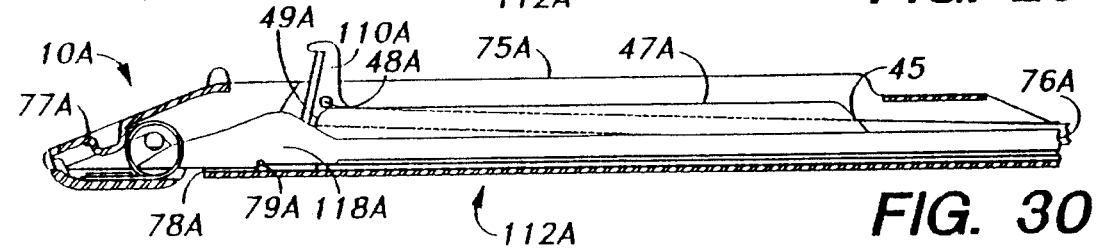
Figure 31:
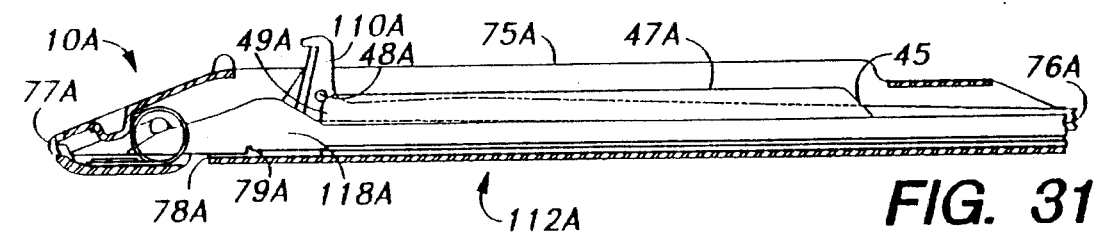
Figure 32:
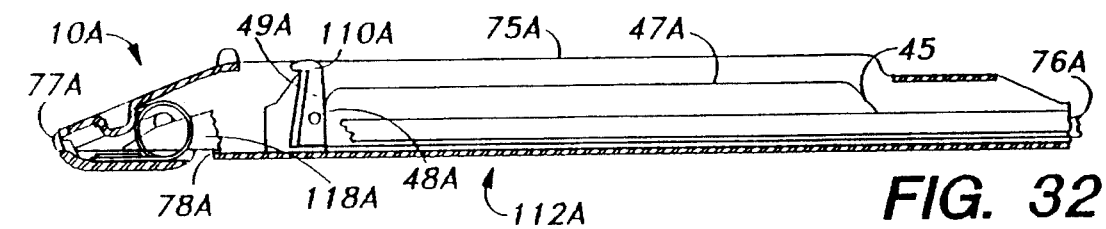
Figure 33:
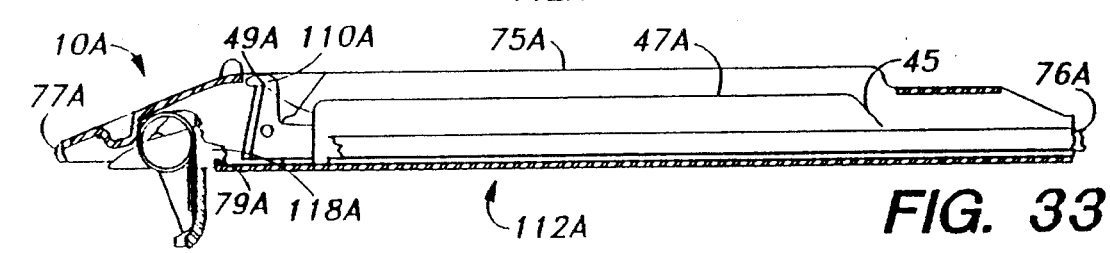

Generally the elongate staple housing 112 defines a vertical direction (the direction of the arrow 76 in FIG. 22). In FIGS. 22–27, the vertical direction is substantially perpendicular to the longitudinal axis of the staple housing 112.

In the preferred embodiment, the trapping means comprises at least one of the pushers 118 (and preferably all four pushers) having an interference member, preferably a hook surface 79, and the staple housing 112 having a trap surface 78 in substantially the distal end portion 77 of the staple housing 112 for receiving the hook surface 79 of the pusher 118 when the pusher 118 is in the fired position. The trapping means also preferably includes a biasing means, such as an interference fit between the pushers 118 and the bottom portion of the staple housing 112 forming the slot 121, for biasing the pushers 118 vertically away (downward in FIG. 22) from the tissue to be stapled and for biasing the hook surface 79 of the pusher 118 into engagement with the trap surface 78 of the staple housing 112. Alternatively, the biasing means may comprise engagement between the camming surface of the pusher 118 and ramped surface 69 of the staple housing 112 which moves the pusher 118 away from the stapled tissue (see FIGS. 26 and 27) so that the hook surface 79 may engage the trap surface 78.

The stapler 10 may optionally include the knife 110 that is mounted for longitudinal movement between pre-fired (FIG. 22) and fired (FIG. 27) positions. The knife 110 is also mounted for vertical movement between a) an extended position (FIG. 22) with the knife 110 projecting vertically beyond the tissue engagement surface 75 of the staple housing 112 so that it may cut tissue between applied rows of staples, and b) a retracted position (FIGS. 26 and 27) with the knife 110 less exposed than in the extended position. Preferably, in the retracted position, at least a substantial portion of the knife 110 is retracted within the staple housing 112 to reduce the risk of exposure of medical personnel who handle the spent housing 112.

To accomplish the longitudinal and vertical movement of the knife 110, the knife 110 may include a generally cylindrical bearing surface 48. The knife is sized and shaped to ride in a guide channel of the staple housing 112. The guide channel has a cutting motion portion 47 for receiving the bearing surface 48 as the knife 110 moves between the pre-fired and fired positions. The guide channel also has an abutment portion 49 situated approximately perpendicular to the cutting motion portion 47 of the guide channel.

When the pushers 118 and knife 110 are in the fired position, the pushers 118 are prevented from moving proximally due to engagement between the hook surface 79 and trap surface 78. In event that the hook surface 79 is inadvertently released from trap surface 78, engagement between abutment portion 49 and the bearing surface 48 of the knife 110 would restrict longitudinal (proximal) movement of the knife 110 from the fired toward the pre-fired position. If the knife 110 and pushers 118 are connected to each other as they typically are, the engagement between abutment portion 49 and the bearing surface 48 of the knife 110 also beneficially prevents return movement of the pushers 118. Preferably, the knife 110 is vertically biased downwardly from the extended toward the retracted position by a biasing means such as an interference fit with surface 47 created during assembly. Once surface 47 is passed, the knife 110 is moved downwardly in the Figures to the retracted position by the biasing means.

While the firing rod 90, pushers 118 and knife may comprise a unitary monolithic element, the firing rod 90, pushers 118 and knife may optionally be associated by means of a one-way coupling 87. The one-way coupling 87 affords reciprocal movement of the firing rod 90 (and firing handle 94) between pre-fired and fired positions. When the stapler includes the trapping means discussed above, the pusher 118 and knife 110 are only movable from the pre-fired to the fired position as the trapping means traps them in the fired position.

FIGS. 37 and 38 illustrate one example of the one way coupling 87. During the movement of the firing rod 90 from the pre-fired toward the fired position, the one-way adapter 87 abuts the knife 110 and pusher 118 assemblies and transmits the firing force to those elements. Once the pushers 118 and knife 110 reach their distalmost position, the pushers 118 and knife 110 are trapped in that position by the trapping means. Because the pushers 118 and knife 110 are trapped, the adapter 87 affords separation of the firing rod 90 from the pushers 118 and the knife 110 when the firing handle 94 is moved from the fired toward the pre-fired position.

This one-way coupling 87 affords repeated movement of the firing handle 94 between the pre-fired and fired positions. However, the difference in resistance to the movement of the firing handle 94 operates as a tactile feedback to the user signalling that the pushers 118 and/or knife 110 have moved to the fired position, and that the staple housing 112 is empty and should be replaced.

The staple housing 112 may optionally include lockout device 50. The structure and function of a lockout device 50 is described in U.S. patent application Ser. No. 08/055,817, entitled, "Laparoscopic Surgical Instrument With a Mechanism For Preventing its Entry Into the Abdominal Cavity Once It Is Depleted and Removed From the Abdominal Cavity", filed Apr. 30, 1993 and naming Claude A. Vidal, Russell J. Redmond and Alan K. Plyley as inventors, the entire contents of which are herein expressly incorporated by reference.

FIGS. 28 through 33 illustrate portions of another embodiment of surgical stapler generally designated by reference character 10A which has many parts that are essentially the same as the parts of the stapler 10 shown in FIGS. 21–27 and which have been identified by the same reference numeral to which the suffix "A" has been added.

Like the stapler shown in FIGS. 21–27, the stapler 10A has a staple housing 112A with tissue engagement surface 75A, proximal 76A and distal 77A end portions and trap surface 78A. The stapler 10A also has a plurality of pushers 118A with hook surfaces 79A. The operation of the pushers 118A is similar to the operation of the pushers 118 described above.

Like the knife 110, the knife 110A includes a knife bearing surface 48A. Like the staple housing 112, the staple housing 112A has a guide channel with a cutting motion portion 47A and abutment portion 49A with similar operations. Unlike the stapler 10, in the stapler 10A, the knife 110A is initially in a retracted position (FIG. 28) which eliminates the need for a protective cover and reduces the exposure of the knife 110A. When the knife 110A is moved from the pre-fired toward the fired position, engagement between the journal surfaces 49A of the knife 110A and a camming surface 45 on the staple housing 112A cam the knife 110A from the retracted toward the projecting position.

Figure 21:
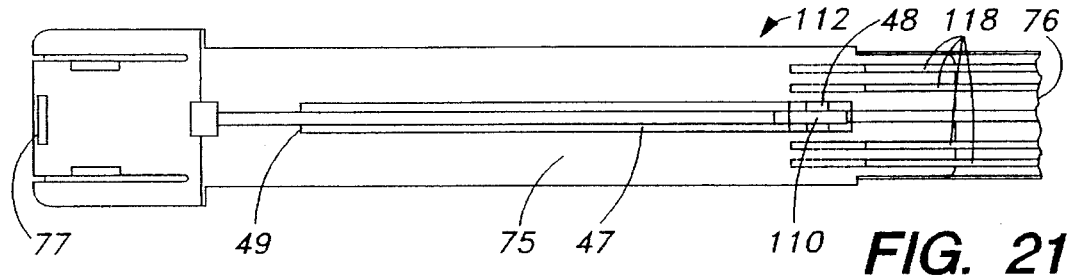
FIG. 21 is a top view of another embodiment of stapler according to the present invention.

Referring now to FIG. 21, the pushers 118 of the stapler 10 are preferably substantially aligned longitudinally to reduce the overall length of the staple housing 112 past the distalmost staple in a row. This arrangement also reduces the longitudinal projection of the stapler 10 past the distal end 19 of the housing 19. Also preferably, the stapler 10 includes four pushers which may be utilized to apply either four or six parallel rows of staples. When the stapler 10 includes six parallel rows of staples, an additional pair of pushers 118 may be added to the stapler or, alternatively, two of the pushers 118 may be required to fire two adjacent rows of staples. As is well known in the art, this may be accomplished by using a plurality of staple drivers each of which are adapted to engage two, adjacent staples in adjacent rows of staples.

One example of a staple pattern 125 that may be applied by the stapler 10 is illustrated in FIG. 16. Staple pattern 125 is substantially symmetrical about the path 85 of the knife 110. If a knife 110 is not present in the stapler 10, reference character 85 refers to the centerline of the six parallel rows of staples.

When the staple pushers 118 are substantially parallel or aligned relative to the longitudinal axis of the stapler (as shown in FIG. 21), a first, preferred embodiment of staple pattern 130 for use in the stapler 10 is shown in FIG. 17. The staple pattern 130 shown in FIG. 17 has a proximal end 131 and a distal end 133. Any line drawn transverse to the longitudinal axis of the staple pattern between the ends 131 and 133 will cross at least three staples. In contrast, lines 129 of pattern 125 only intersect two staples.

When the staple pushers 118 are substantially parallel or aligned relative to the longitudinal axis of the stapler, the staple pattern 130 is preferred to the staple pattern 125 as, with the staple pattern 130, the pushers 118 are not required to simultaneously overcome the initial maximum formation force of more than three staples. In contrast, with the staple pattern 125, the initial maximum formation force of first two, then four, then two etc. . . . staples are encountered by the pushers. This is believed to increase the resultant maximum force encountered by a surgeon. It is also believed to contrubute to an inconsistent firing force experienced by the surgeon as the surgeon fires the staple line.

A second, preferred embodiment of staple pattern for the stapler 10 is shown in FIG. 34 and generally designated 140. That staple pattern has a proximal end 141 and a distal end 142, and six adjacent rows numbered 151–156. The staple to staple spacing within each row is substantially identical and is defined as the pitch. Each of the rows 151–156 is longitudinally offset from an adjacent row by a fraction of the pitch. For example, row one 151 may be offset from row two 152 by ½ of the pitch. The third row 153 is preferably offset one half of the offset distance of rows one 151 and two 152 (e.g. ¼ of the pitch). The staple line 140 is symetrical about the centerline or knife travel line 85.

The centerline 85 separates the staple rows 151–156 into a first set 151–153 and a second set 154–156. Each of the rows in the first set 151–153 are offset from the other two rows in the first set. Additionally, each of the rows in the second set 154–156 are offset from the other two rows in the second set. However, note that row 151 is not longitudinally offset from row 154. Instead, rows 151 and 154 are longitudinally aligned. Preferably, the first set of rows 151–153 is a mirror image of the second set of rows 154–156 about the centerline 85.

Figure 35:
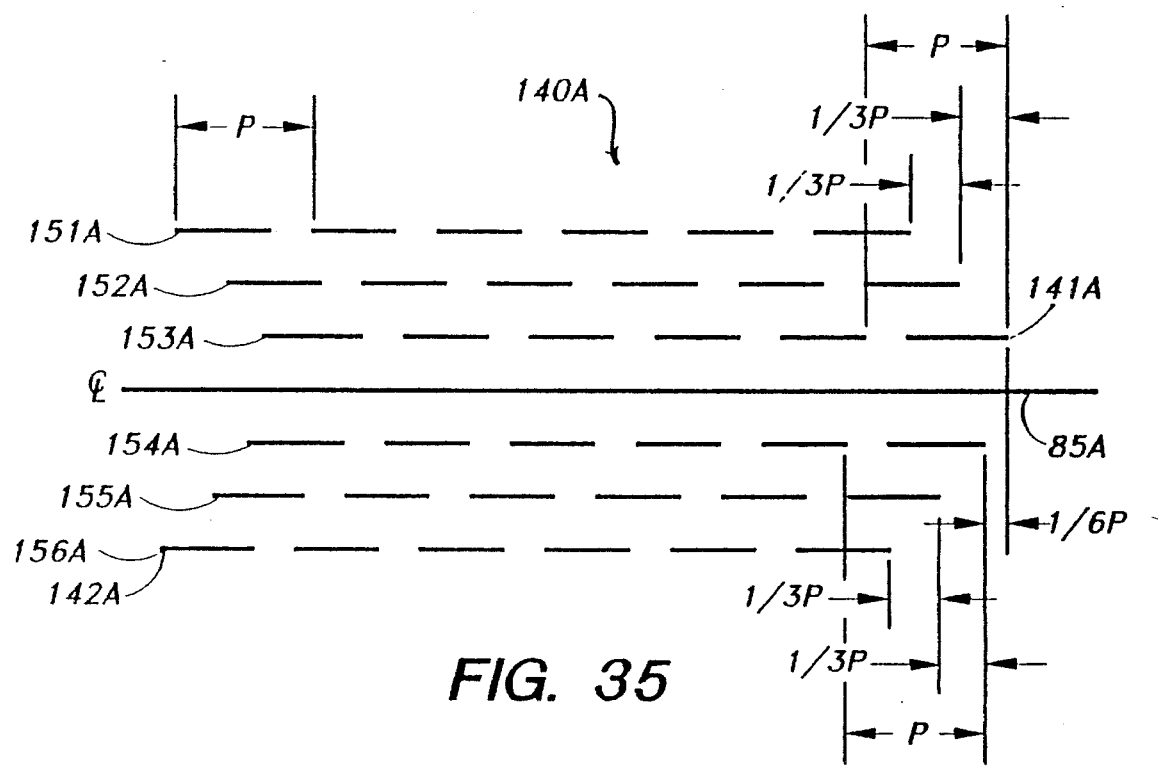

A third preferred embodiment of staple pattern for the stapler 10 is shown in FIG. 35 and generally designated 140A. That staple pattern has a proximal end 141A and a distal end 142A, and six adjacent rows numbered 151A–156A. Each of the rows 151A–156A is longitudinally offset from all of the other rows in the pattern including adjacent rows.

The staple to staple spacing within each row 151A–156A is identical and is illustrated as P, the staple row pitch. On each half of the cartridge centerline 85A the two pairs of three rows (151A–153A and 154A–156A) are longitudinally offset relative to an adjacent row by ⅓ of the pitch (⅓×P). Rows 153A and 154A are offset by ½ of this amount, or ⅙ of the pitch (⅙× P).

When the staple pushers 118 are substantially parallel or aligned relative to the longitudinal axis of the stapler, the staple pattern 140A is preferred from a firing force standpoint to the staple pattern 125 because the pushers 118 do not encounter more than one initial maximum formation force at the same time. By separating the occurrences of the maximum formation forces, the overall force encountered by the surgeon is reduced and the forces are smoother (more uniform and constant) than the pattern 125.

The preferred staple row pitch is about 0.156 inches. The longitudinal offset between rows 151A and 152A is preferably about 0.052 inches. Between rows 152A and 153A the preferred offset is about 0.052 inches. The longitudinal offset between rows 153A and 154A is about 0.026 inches and the offset between rows 154A and 155A as well as between rows 155A and 156A is preferably about 0.052 inches. The distance between backspans in adjacent rows is preferably about 0.040 inches. The distance between rows 153A and 154A is preferably about 0.080 inches to provide room for movement of the knife along axis 85A.

Figure 36:
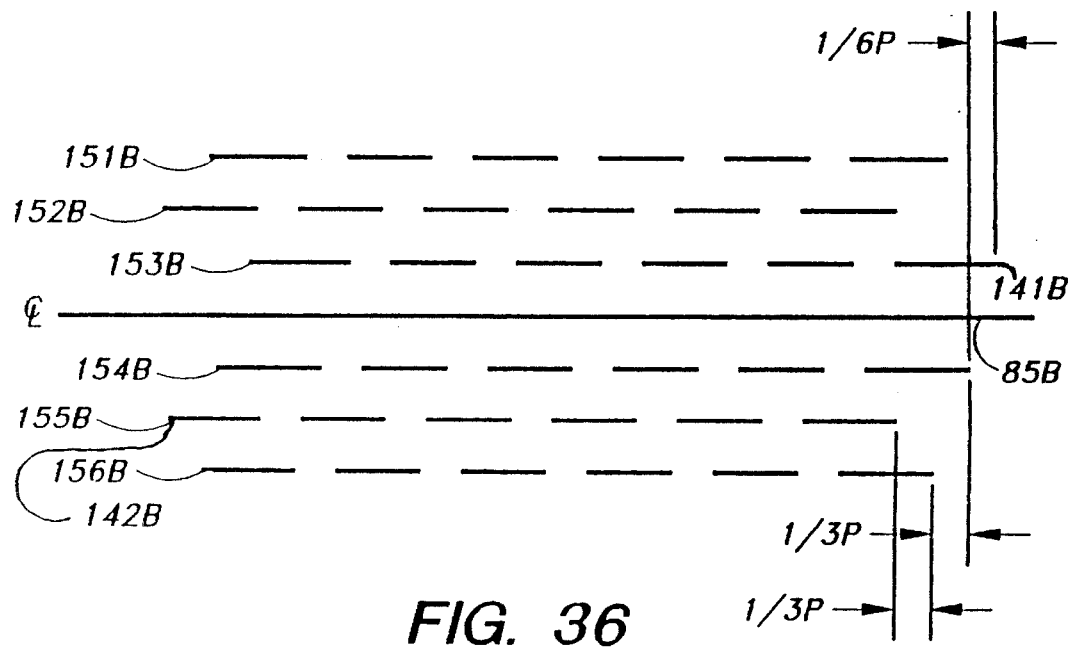
FIG. 36 is a schematic view of portions of a fourth embodiment of staple rows according to the present invention which illustrates six parallel rows of staples in a pattern.

A fourth preferred embodiment of staple rows according to the present invention is shown in FIG. 36. Like the pattern 140A, in the pattern shown in FIG. 36, the staple to staple spacing within each row 151B–156B is identical and is defined as P, the staple row pitch. The pattern has a pair of ends including proximal end 141B and distal end 142B. Also like the pattern 140A, in the pattern shown in FIG. 36, each of the rows 151B–156B are offset relative to all of the other rows in the pattern.

Assuming that pitch remains constant, FIGS. 35 and 36 illustrate two of several combinations of stagger patterns according to the present invention. Generally speaking, the force considerations between the rows shown in FIGS. 35 and 36 are similar, but one stagger pattern may have desirable clinical advantages over another.

Figure 43:
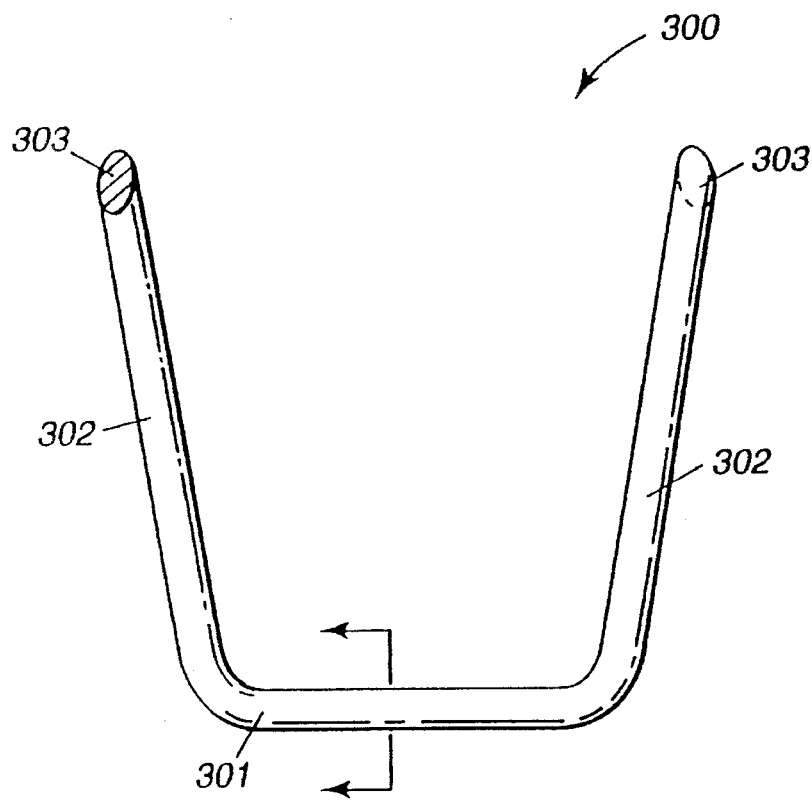
FIG. 43 is a side view of a first embodiment of an optional, unformed staple for use in the stapler according to the present invention.

FIGS. 43–48 and 50–52 illustrate optional embodiments of staples for use with the staplers of the present invention which are believed to restrict the amount of the third maximum formation force mentioned in the Background section of this document. FIG. 43 illustrates a first optional embodiment of staple 300 for use with the staplers according to the present invention which is believed to be particularly useful for stapling thin tissue. The staple 300 has a backspan 301, and legs 302 with tips 303. Unlike prior art tips which are created by a blanking operation that occurs at an angle perpendicular to the plane of the staple, the tips 303 are formed from a blanking process which is significantly less than perpendicular to the plane of the staple. The tips 303 present an edge contact to the anvil dimple and more importantly to the backspan when it is crimped over thin tissue. This edge contact affords easy slide off of the staple top face from the backspan 301 which reduces the third maximum formation force.

Figure 43A:
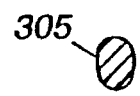
FIG. 43A is a first example of a cross-section taken about the cross section lines of FIG. 43.
Figure 43B:
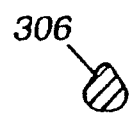
FIG. 43B is a second example of a cross-section taken about the cross section lines of FIG. 43.
Figure 43C:
FIG. 43C is a third example of a cross-section taken about the cross section lines of FIG. 43.
Figure 44:
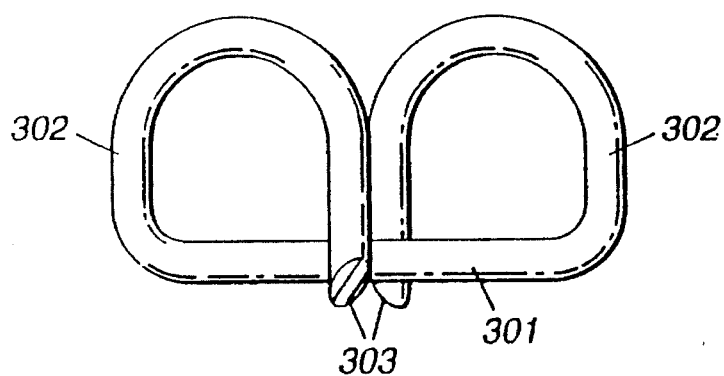
FIG. 44 is a side view of the staple of FIG. 43 in a formed condition.

FIGS. 43A–43C illustrate optional cross-sections which may be coined into the backspan 301. FIG. 43A illustrates an oval cross-section 305, FIG. 43B a triangular or offset ramp cross-section 306, and FIG. 43 illustrates an arcuate cross-section 307 with a cam angle surface. These enhancements are believed to cause the deflecting tip 303 to move away from the backspan 301 at a much lower force than the prior art flattened backspan.

Figure 45:
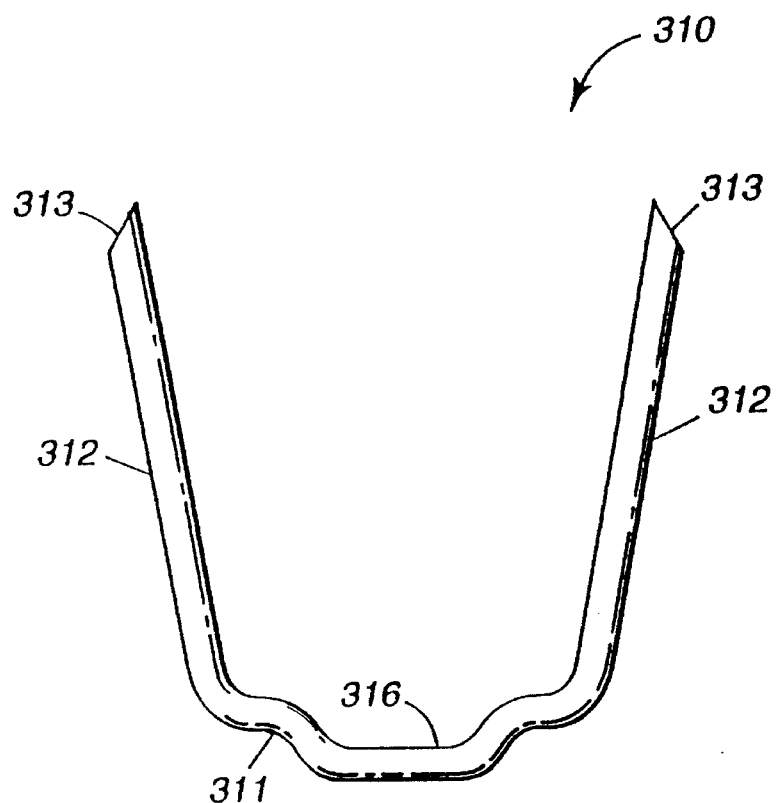
FIG. 45 is a side view of a second embodiment of an optional, unformed staple for use in the stapler according to the present invention.
Figure 46:
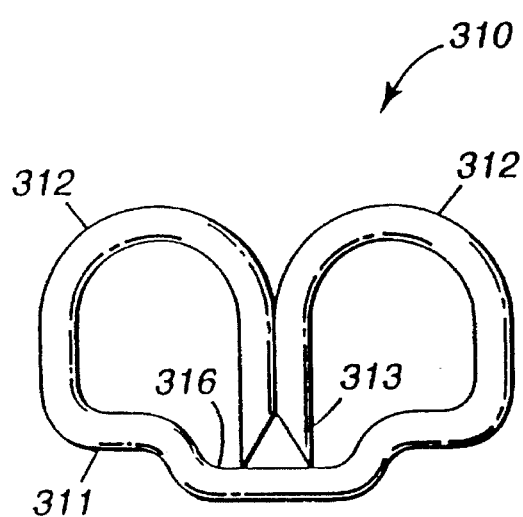
FIG. 46 is a side view of the staple of FIG. 45 in a formed condition.

FIGS. 45 and 46 illustrate a second embodiment of optional staple 310 for use with a stapler according to the present invention. The staple 310 includes a backspan 311 with a groove 316, and legs 312 with tips 313. The groove 316 which is shown in only one of many potential shapes (i.e. square, triangular, bowed, etc.) provides additional travel for the staple tips 313 in order to prevent contact with the backspan 311 even in thin tissue. This groove 316 would also serve to stabilize the staple 310 as it nests in a molded slot in the driver.

Figure 47:
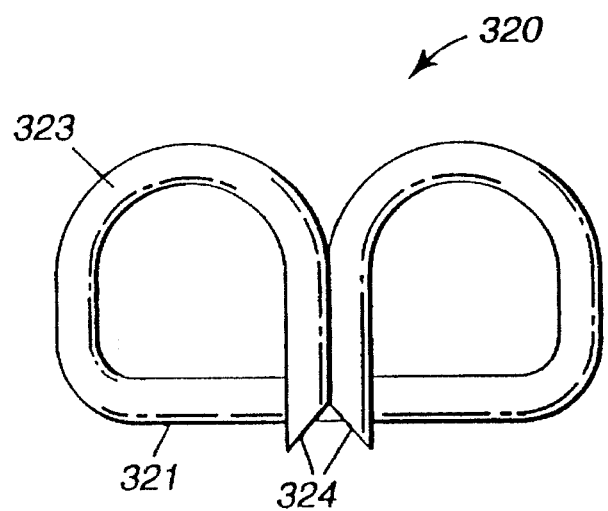
FIG. 47 is a side view of a third embodiment of optional formed staple for use in the stapler according to the present invention.
Figure 48:
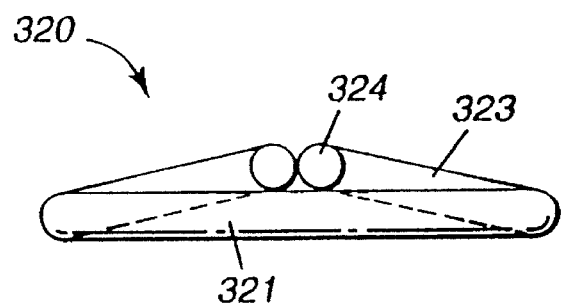
FIG. 48 is a top view of the staple of FIG. 47.
Figure 49:
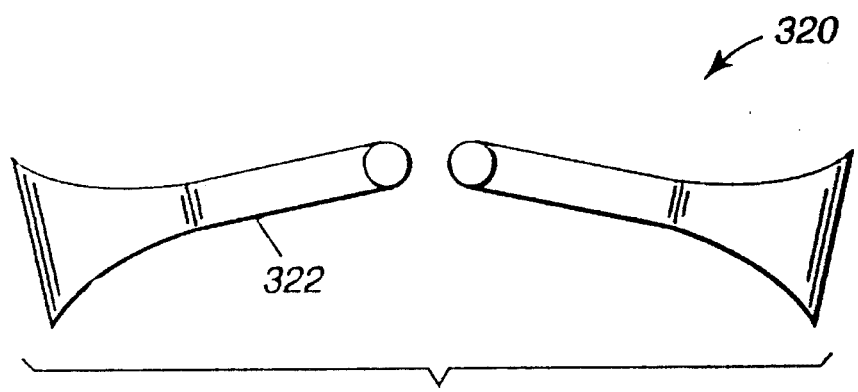
FIG. 49 is a plan view of a dimple of an anvil for forming the staple of FIG. 48.

FIGS. 47 and 48 illustrate a third embodiment of optional staple 320 for use with the stapler according to the present invention. The staple 320 includes a backspan 321, legs 323 and tips 324. FIG. 49 illustrates an anvil dimple 322 that is fabricated at a slightly offset angle to the staple line axis. This combination always forces the staple tips to the same side of the backspan and helps to reduce the third maximum formation force. Notably, if the sides of the anvil dimple shown in FIG. 49 are substantially parallel but offset from the firing direction, then the anvil dimple may assist in forming the staple shown in FIG. 44.

Figure 50:
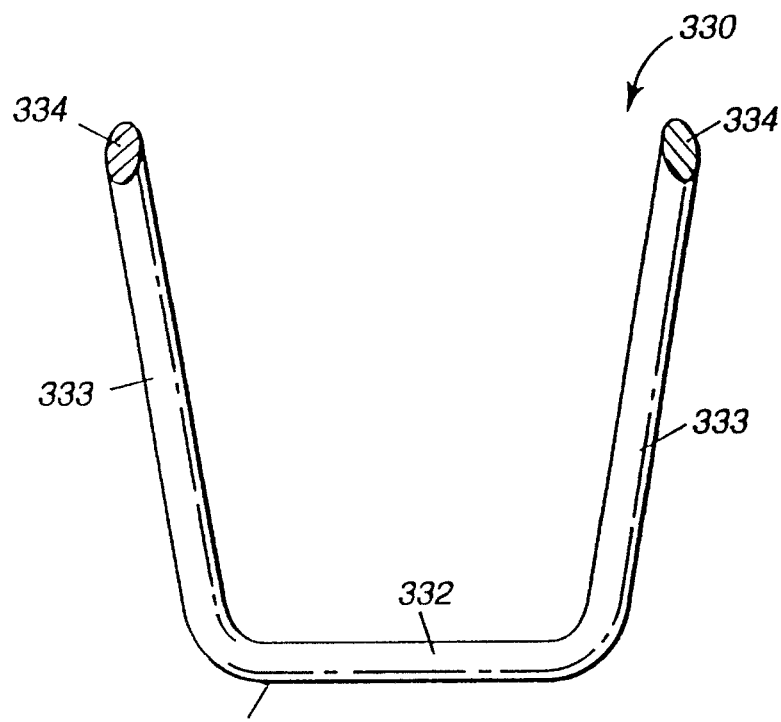
FIG. 50 is a side view of a fourth embodiment of an optional, unformed staple for use in the stapler according to the present invention.
Figure 51:
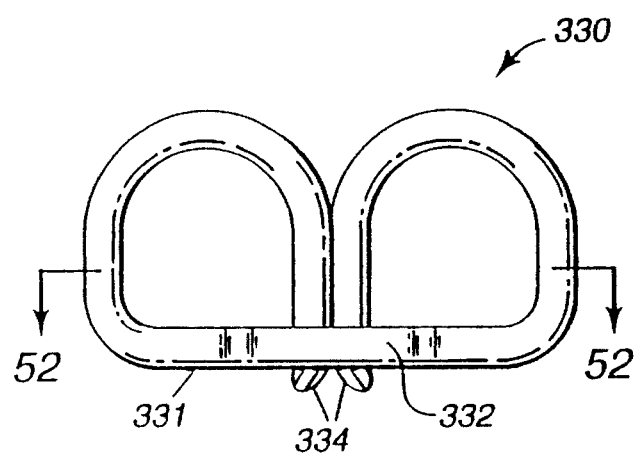
FIG. 51 is a side view of the staple of FIG. 50 with the staple in a formed condition.
Figure 52:
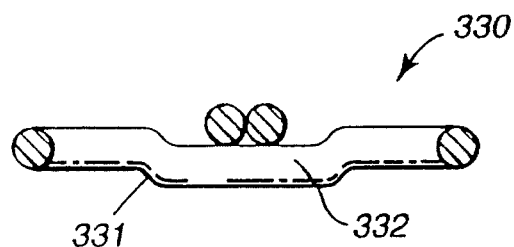
FIG. 52 is a sectional view of the staple of FIG. 51 taken approximately along lines 52—52 of FIG. 51.

FIGS. 50–52 illustrate a fourth embodiment of optional staple 330 for use with the staplers according to the present invention. The staple includes a backspan 331 with a lateral displacement 332, and legs 333 with tips 334. This feature allows the tips 334 of the staple 330 to avoid contact with the backspan 331 when used with a prior art dimple. Although the amount of offset may be practically limited by the width of the staple housing staple slot, there may be sufficient room to displace the backspan at least one-half of the staple wire diameter.

Optionally, the stapler 10 may include a flushing channel 9 having a flush port 3 (FIG. 1). If the stapler 10 comprises a reusable stapler designed to be sterilized, the flushing port 3 may assist in cleaning and sterilizing the internal elements of the stapler 10.

FIGS. 6 through 12 and 41 illustrate portions of another embodiment of surgical stapler generally designated by reference character 200 which has many parts that are essentially the same as the parts of the stapler 10 shown in FIGS. 1–5 which have been identified by the same reference numeral to which the suffix "B" has been added.

The proximal portion of the stapler 200 is substantially identical to the proximal portion of the stapler 10 except that the stapler 200 does not have a torsion spring 31. Like the stapler 10, the stapler 200 has cartridge and anvil retention portions 14B and 16B. A significant difference between the staplers 10 and 200 is that the stapler 200 has a different approximation means than the stapler 10. Like the stapler 10, the approximation means of the stapler 200 comprises three assemblies which are best seen in FIGS. 8 and 10–12.

The first assembly comprises a cartridge frame 22B that is fixedly mounted relative to the housing 17B in a manner such that the cartridge frame 22B does not move relative to the housing 17B. Of course, like the stapler 10, in the stapler 200, the housing 17B may rotate relative to the proximal portion of the stapler, but the housing 17B does not move longitudinally or rotate relative to the cartridge frame 22B. The cartridge frame 22B has opposite first and second side bearing surfaces 23B and 25B which are laterally spaced about the longitudinal axis of the stapler 200.

Figure 7:
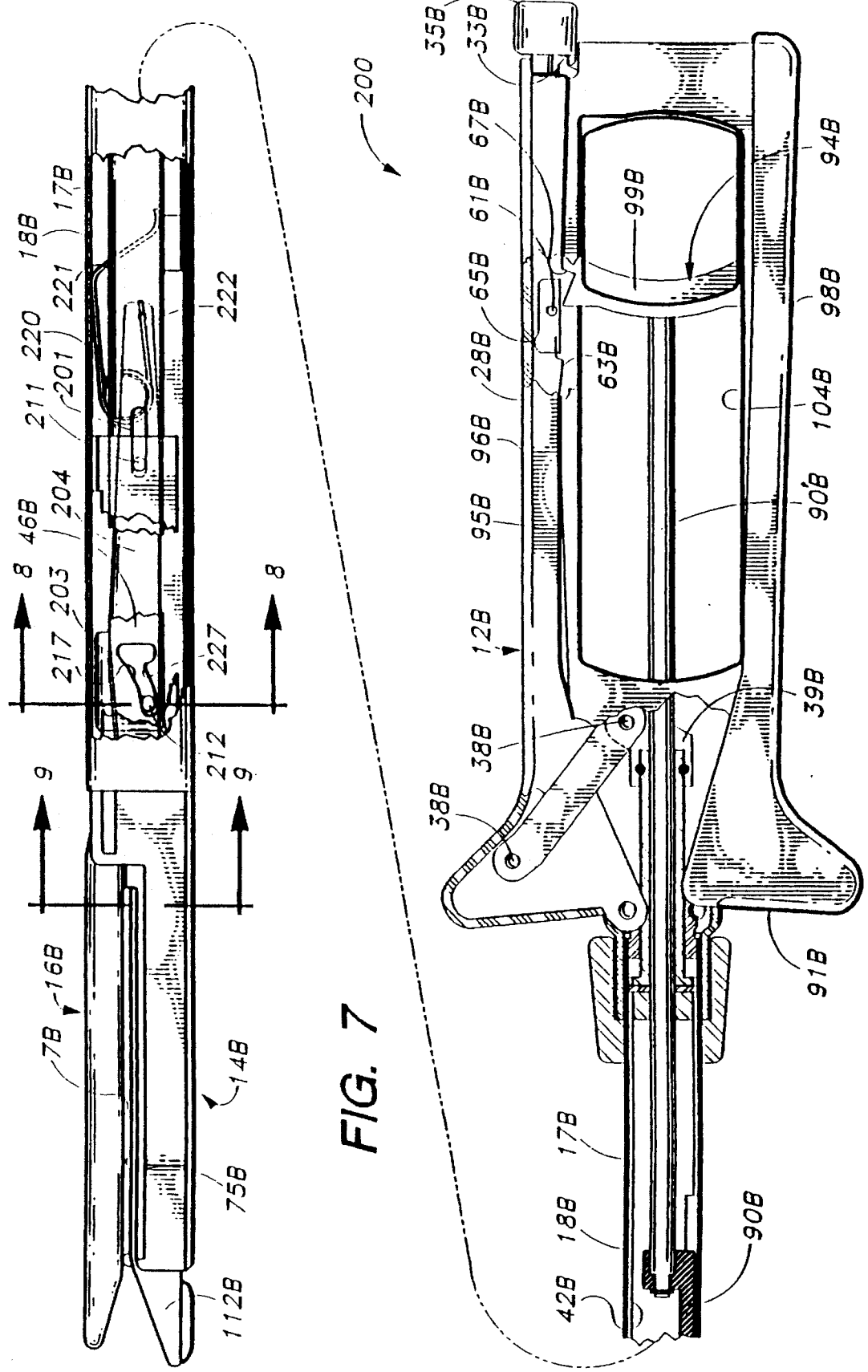
FIG. 7 is a side view of the stapler of FIG. 6 with the cartridge and anvil of the stapler in a closed position.
Figure 8:
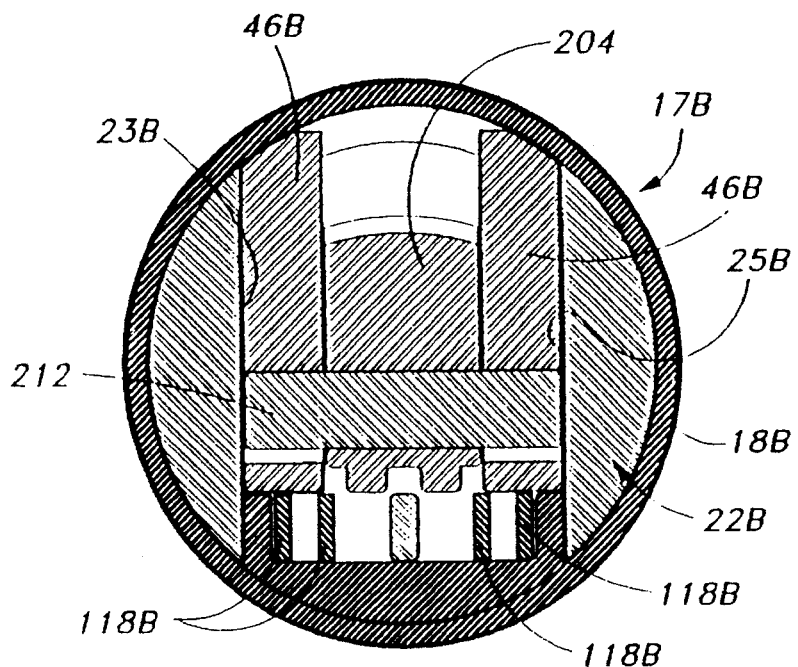
FIG. 8 is a sectional view of the stapler of FIG. 7 taken approximately along lines 8—8 of FIG. 7.
Figure 11:
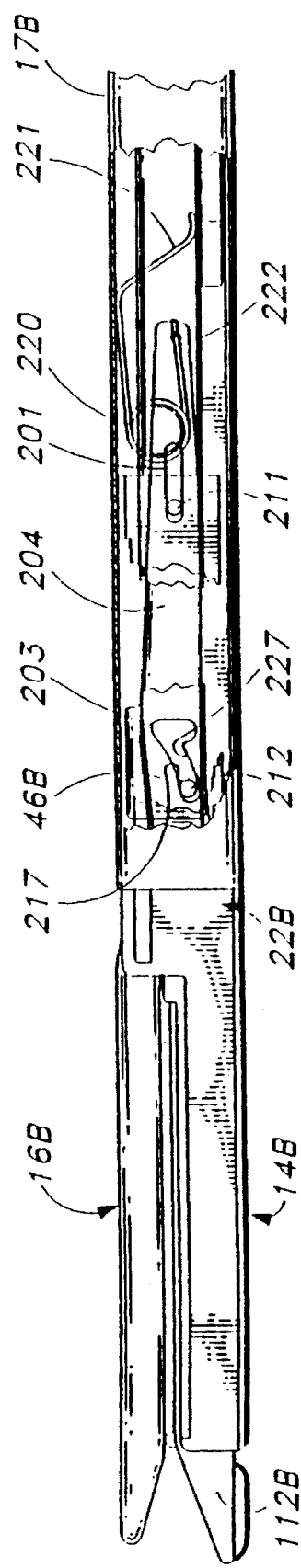
FIG. 11 is an enlarged side view of a distal portion of the stapler of FIG. 7.

The second assembly of the approximation means for the stapler 200 comprises a longitudinal movable assembly. The longitudinal movable assembly is operatively associated with locking lever 28B and control shaft 42B and is movable between an open position (FIGS. 6 and 10) and a closed position (FIGS. 7 and 11).

A clevis (similar to the clevis 44 shown in FIG. 5A) fixedly attaches a pair of transversely spaced guide members 46B to the control shaft 42B so that the guide members 46B do not move relative to the control shaft 42B. The first and second bearing surfaces 23B and 25B of the cartridge frame 22B receive and abut their respective guide members 46B and assist in constraining the guide members 46B to substantially axial longitudinal movement relative to the housing 17B and cartridge frame 22B.

The guide members 46B each have a first, proximal control groove 201 and a second, distal control groove 203. To close the stapler 200, the control shaft 42B is moved proximally from the position in FIG. 6 to the position in FIG. 7 substantially linearly and parallel to the axis of the stapler 200. Reversing the direction of the control shaft 42B (e.g. distal movement of the shaft 42B) opens the stapler 200.

The third assembly of the approximation means of the stapler 200 comprises an anvil assembly which includes the anvil retention portion 16B. The anvil assembly includes a proximal portion 204 sandwiched between guide members 46B and terminating in a proximal end. The anvil assembly also has a distal end. Proximal post 211 and distal post 212 project laterally or transversely from spaced positions on the sides of the proximal portion 204 and are fixedly attached to the proximal portion of the anvil 204.

The proximal post 211 is sized and shaped to be received in the substantially longitudinally extending slot 201 of the guide member 46B. The proximal post 211 affords pivotal movement of the anvil relative to the guide member 46B. The distal post 212 is sized and shaped to be received in the slot 203. The post 211 is mounted in the anvil and indexed into the cartridge frame 22B. The post 211 restricts longitudinal movement of the anvil relative to the housing 17B and cartridge frame 22B.

The stapler 200 includes a torsion spring 220 having first 221 and second 222 ends. The first end 221 abuts the housing 17B and the second end abuts the proximal portion 204 of the anvil. The torsion spring 220 biases the anvil toward the open position. Latch 33B engages retention surfaces on release lever 35B to secure the locking lever 28B in the closed position against the bias of torsion spring 220. Preferably, in the embodiment shown, the spring 220 does not communicate with the lever 28B.

The torsion spring 220 provides an indexing location for a disposable cartridge pusher assembly. The torsion spring 220 also provides a detent for the cartridge/staple housing as it is inserted. The spring 220 provides a detent to give the user a tactile 'click' when cartridge/staple housing has been properly inserted.

The shapes of the first and second control grooves or slots 201 and 203 control the motion of the anvil retention portion 16B as it moves from an open to a closed position. Preferred shapes of the slots 201 and 203 are illustrated. The groove 201 extends substantially longitudinally and affords pivotal movement of the anvil relative to the guide member 46B about post 211.

Figure 12:
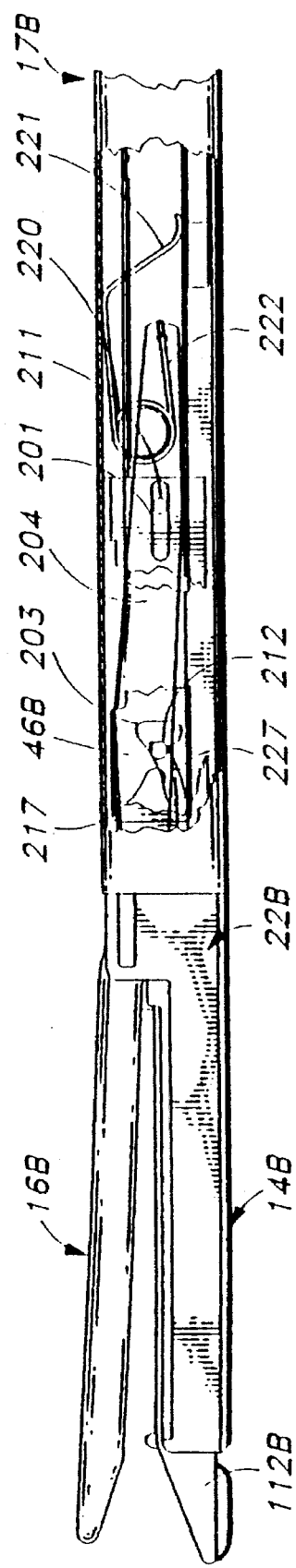
FIG. 12 is an enlarged side view of the second embodiment of surgical stapler according to the present invention with the cartridge and anvil in an emergency open position.

The groove 203 includes closing cam portion 217 which cams the post 212 (and thus the cartridge retention portion 16B) to the closed position when the guide members 46B are moved proximally relative to the anvil. The groove 203 also has positive opening cam portion 227. FIG. 12 illustrates the anvil retention portion 16B and the cartridge retention portion 14B in an emergency open position. If for any reason the anvil retention portion 16B and the cartridge retention portion 14B do not move from the closed toward the open position under the bias of torsion spring 220, the positive opening cam portion 227 may be used to positively cam the anvil retention portion 16B and the cartridge retention portion 14B toward the open position. To use the positive opening cam portion 227, the surgeon merely moves the lever lock 28B from the position in FIG. 7 toward the position in FIG. 6.

Figure 39:
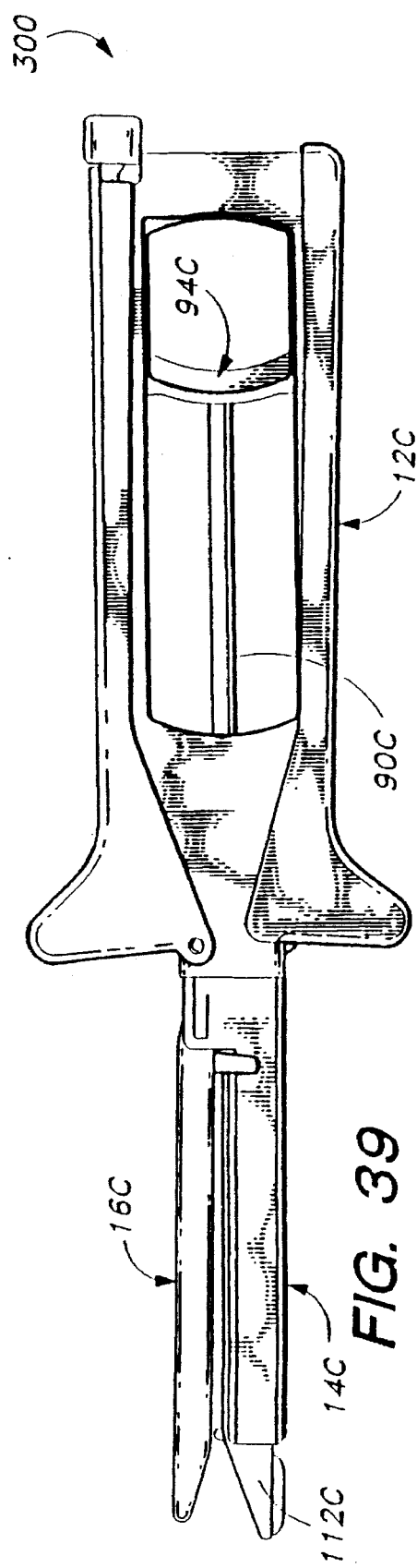
FIG. 39 is a schematic view of a surgical stapler for use in an open surgical procedure that may include several aspects of the present invention, which illustrates the cartridge and anvil of the stapler in a closed position.
Figure 40:
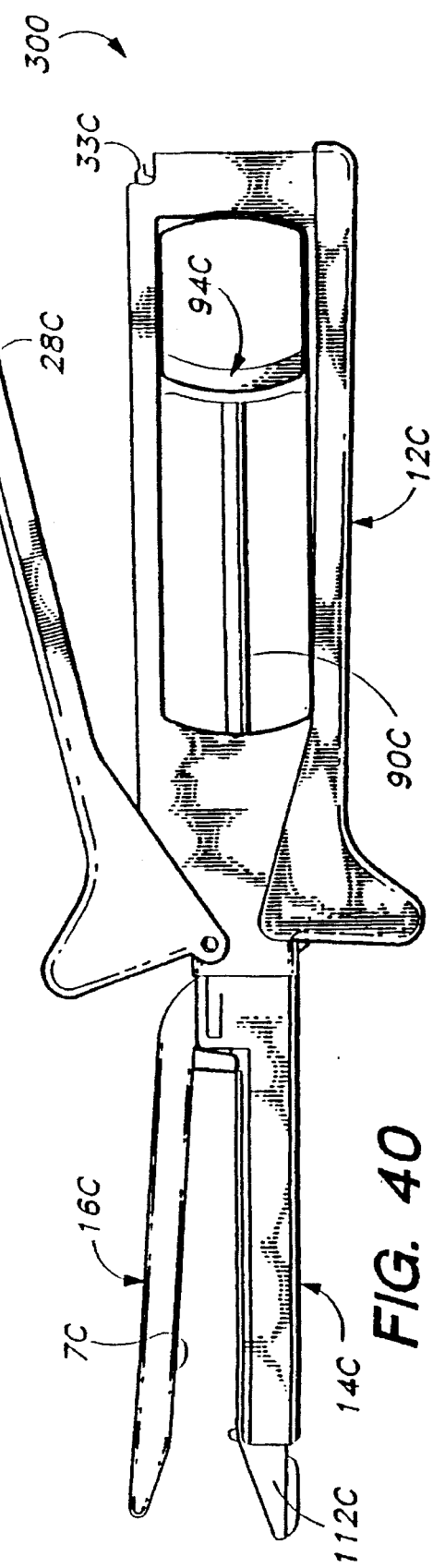
FIG. 40 is a schematic view of the stapler of FIG. 39 which illustrates the cartridge and anvil of the stapler in a closed position.
Figure 41:
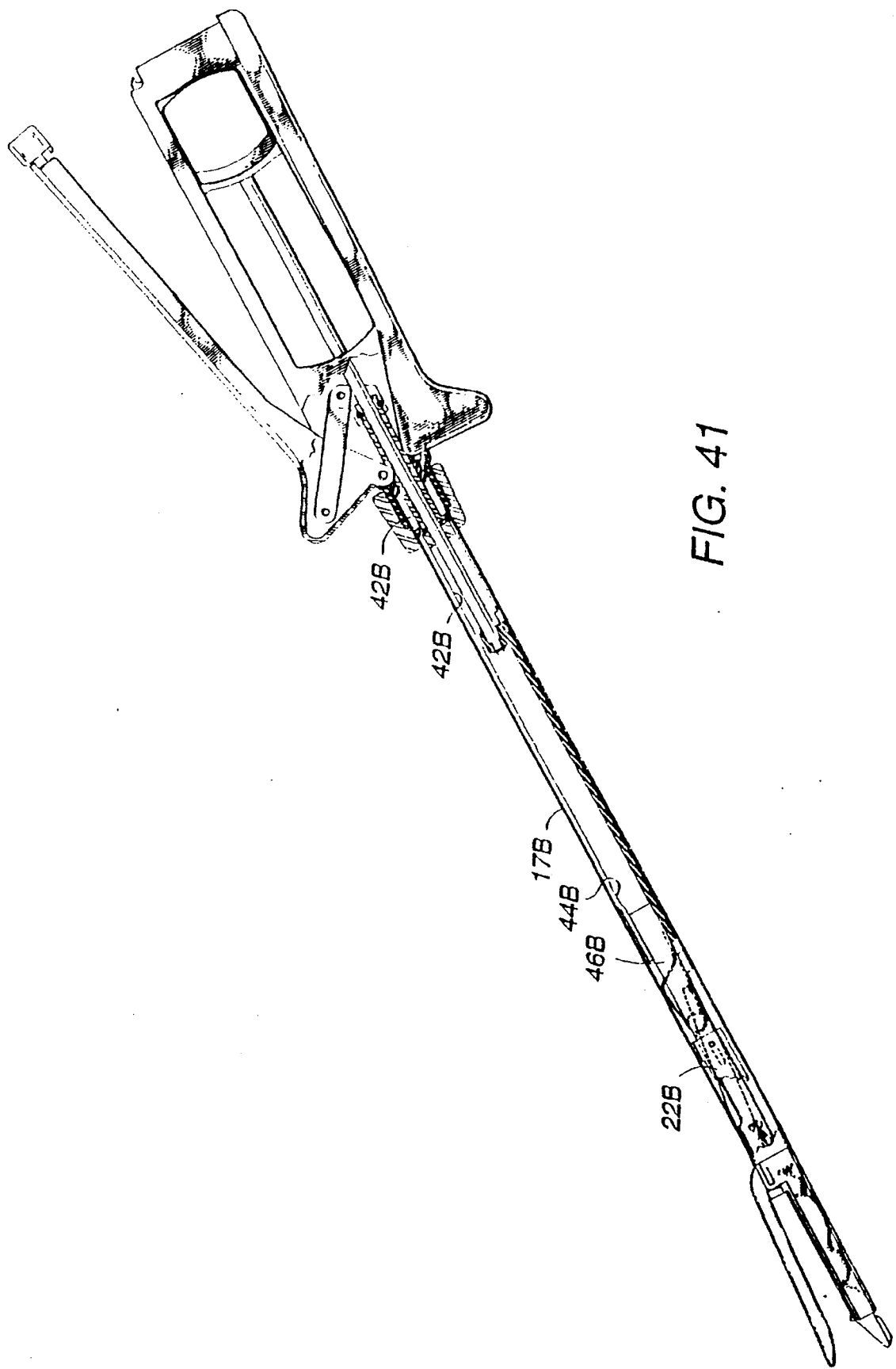
FIG. 41 is a side view of the surgical stapling instrument of FIGS. 6 and 7 which illustrates the proximal and distal ends of the stapler at the same size.

While the staplers 10 and 200 comprise staplers for use in a laparoscopic surgical procedures, it should be noted that many of the features and devices disclosed herein may be used in a stapler designed for use in an open surgical procedure. FIGS. 39 and 40 illustrate a stapler 300 for use in an open surgical procedure.

The stapler 300 may be substantially identical to the stapler 10, except that the relatively long housing portion 17 is replaced by a very short portion and preferably, the stapler 300 would comprise first and second separable parts (not shown) which is typical for surgical staplers used in open surgical procedures. Like the stapler 10, the stapler 300 includes cartridge and anvil retention portions 14C and 16C, similar approximation means, a staple housing 112C, firing handle 94C, firing rod 90C, latch 33C and release lever 35C.

The stapler 300 optionally includes a firing assembly generally identical to the firing assembly illustrated in FIGS. 1–3, 13–15 and 19–20 and includes a firing handle 94C, firing rod 90C and the pusher assembly generally identical to the pusher assembly shown in FIGS. 13–15 which include pushers 118 with linear cam surfaces 1–3. The stapler 300 may optionally place staples in any of the patterns illustrated in FIGS. 17 and 34–36. Additionally, the stapler 300 may also include the trapping means illustrated in FIGS. 21–27 and 28–33.

The materials used to construct the staplers according to the present invention may comprise any materials suitable for use in surgical devices. Such materials are widely known to those skilled in the art. Examples of medical grade materials include particular grades of stainless steel and plastics.

The present invention has now been described with reference to several embodiments thereof. It will be apparent to those skilled in the art that many changes can be made in the embodiment described without departing from the scope of the present invention. For example, the staplers 10 and 200 may incorporate the overload sensor and lockout device as disclosed in U.S. patent application Ser. No. 08/237,004, filed on the same day as the present application and naming Claude A. Vidal, Alan K. Plyley and Roger Lagerquist as inventors. Additionally, either the individual staples and/or the anvil may be coated to reduce the firing forces encountered by the surgeon. Potential coatings include Teflon, diamond like carbon and tungsten disulfide (Dicronite). Optionally, the staples may be clad with the same material as the anvil to reduce any potential cold welding problems. Thus the scope of the present invention should not be limited to the structure described in this application, but only by structures described by the language of the claims and the equivalents of those structures.

What is claimed is:

1. A surgical stapler for applying staples to compressed tissue comprising:

a handle portion having surfaces adapted to be manually grasped by a surgeon;

a cartridge retention portion and an anvil retention portion, means for mounting said cartridge retention portion and said anvil retention portion for relative movement between a closed position in which said cartridge retention portion and said anvil retention portion are in closely spaced relationship for clamping tissue to be stapled therebetween and an open position in which said cartridge retention portion and said anvil retention portion are spaced farther from each other than in the closed position, an anvil having a plurality of specially shaped surfaces, said cartridge retention portion having a staple housing for enclosing a plurality of staples in substantially parallel, linear rows, each of said staples having a backspan and a pair of legs projected from said backspan, said legs adapted to be buckled during formation of the staples, staple drivers adjacent staples, and a plurality of pushers each having at least three linear camming surfaces, said staple housing being elongate to define a longitudinal axis, said staple housing having a plurality of longitudinally extending pusher slots adapted to receive said pushers to afford movement of said pushers in a firing direction between pre-fired and fired positions, and a plurality of driver channels for receiving said staple drivers to afford movement of said staple drivers in a staple driving direction between pre-eject and ejected positions;

each of said staple drivers having a cam follower surface for engaging the at least three linear camming surfaces of each pusher to move the staple driver from the pre-eject toward the ejected position to substantially sequentially eject the staples from the staple housing and press the ejected staples against the specially shaped surfaces of the anvil to engage, form and close staples in tissue clamped between the staple housing and the anvil, said at least three linear camming surfaces of said pushers comprising:
  a) a first camming surface for engaging a staple driver during initial tissue penetration of a staple, said first camming surface forming a first included angle with the staple driving direction;
  b) a second camming surface for engaging a staple driver during buckling of the legs of a staple, said second camming surface forming a second included angle with the staple driving direction that is greater than said first included angle,
  c) a third camming surface for engaging a staple driver after the legs of a staple have been initially buckled and during the closing of the staple in tissue, said third camming surface forming a third included angle with the staple driving direction that is different than said first and second included angles.

2. A surgical stapler for applying staples to compressed tissue according to claim 1 wherein the first included angle is between about forty-five (45) degrees and about sixty (60) degrees.

3. A surgical stapler for applying staples to compressed tissue according to claim 2 wherein the first included angle is about sixty (60) degrees.

4. A surgical stapler for applying staples to compressed tissue according to claim 1 wherein the second included angle is between about seventy-three (73) degrees and about seventy-eight (78) degrees.

5. A surgical stapler for applying staples to compressed tissue according to claim 4 wherein the second included angle is about seventy-five (75) degrees.

6. A surgical stapler for applying staples to compressed tissue according to claim 1 wherein the third included angle is between about sixty-seven (67) degrees and about seventy-two (72) degrees.

7. A surgical stapler for applying staples to compressed tissue according to claim 6 wherein the third included angle is about sixty-nine (69) degrees.

\* \* \* \* \*